United States Patent
Oths et al.

(10) Patent No.: US 10,745,502 B2
(45) Date of Patent: Aug. 18, 2020

(54) POLYMERS FOR ORAL CARE COMPOSITIONS

(71) Applicant: ISP INVESTMENTS LLC, Wilmington, DE (US)

(72) Inventors: Philip John Oths, Mendham, NJ (US); Karyn B. Visscher, Morris Plains, NJ (US); Fu Chen, Somerville, NJ (US); Petros Gebreselassie, Whitehouse Station, NJ (US); William E. Prosise, Ramsey, NJ (US); Shafiq Sahar Wahidi, Pomona, NY (US)

(73) Assignee: ISP INVESTMENTS LLC, Wilmington, DE (US)

( * ) Notice: Subject to any disclaimer, the term of this patent is extended or adjusted under 35 U.S.C. 154(b) by 0 days.

(21) Appl. No.: 15/777,813

(22) PCT Filed: Nov. 14, 2016

(86) PCT No.: PCT/US2016/061826
§ 371 (c)(1),
(2) Date: May 21, 2018

(87) PCT Pub. No.: WO2017/087319
PCT Pub. Date: May 26, 2017

(65) Prior Publication Data
US 2018/0346628 A1    Dec. 6, 2018

Related U.S. Application Data

(60) Provisional application No. 62/258,024, filed on Nov. 20, 2015.

(51) Int. Cl.
*C08F 220/36*  (2006.01)
*A61Q 11/00*   (2006.01)
(Continued)

(52) U.S. Cl.
CPC ............ *C08F 220/36* (2013.01); *A61K 8/817* (2013.01); *A61K 8/8152* (2013.01);
(Continued)

(58) Field of Classification Search
CPC ....... A61Q 11/02; A61Q 11/00; C08F 220/36; C08F 220/28; C08F 226/10;
(Continued)

(56) References Cited

U.S. PATENT DOCUMENTS

2005/0202362 A1* 9/2005 Ostler ................. A61C 19/063
                                                        433/26
2010/0130641 A1* 5/2010 Findlay .................... C08F 2/38
                                                        523/205
(Continued)

OTHER PUBLICATIONS

International Search Report, PCT/US2016/061826 published on May 26, 2017.

*Primary Examiner* — Blessing M Fubara
(74) *Attorney, Agent, or Firm* — William J. Davis; Nathalie Tietcheu

(57) ABSTRACT

The present invention provides a water-soluble or water-dispersible polymers. The water-soluble or water-dispersible polymer comprise a first monomer having hydrogen bonding/complexing properties to polyphenols, a second monomer having detergent properties, and a third monomer having hydrogen bonding/complexing properties to polyphenols, wherein the first monomer and the third monomer are the same or different. The present invention also provides oral care compositions comprising the water-soluble or water-dispersible polymers. The present invention also provides methods of cleaning, Whitening arid polishing natural teeth and dental prosthesis and of preventing, reducing or removing surface deposited stains from teeth by administering the oral care compositions. The water-soluble or water-dispersible polymer has a structure:

(Continued)

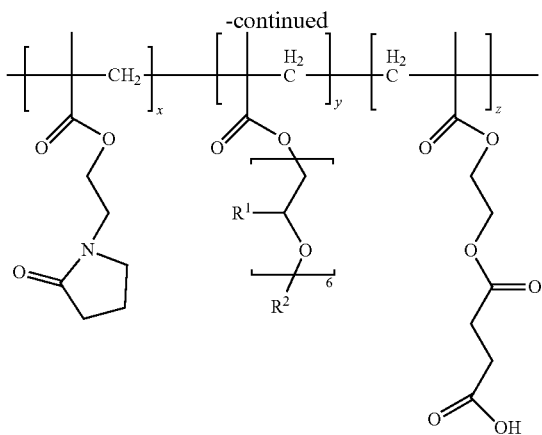

wherein x, y, z, mole %, n, $R^1$, and $R^2$ are defined herein.

7 Claims, 3 Drawing Sheets

(51) Int. Cl.
  *C08F 226/10* (2006.01)
  *A61K 8/81* (2006.01)
  *A61Q 11/02* (2006.01)
  *C08F 220/28* (2006.01)

(52) U.S. Cl.
  CPC ............ *A61K 8/8182* (2013.01); *A61Q 11/00* (2013.01); *A61Q 11/02* (2013.01); *C08F 220/28* (2013.01); *C08F 226/10* (2013.01); *C08F 220/286* (2020.02)

(58) Field of Classification Search
  CPC ............. C08F 220/286; C08F 220/302; A61K 8/8182; A61K 8/8152; A61K 8/817
  See application file for complete search history.

(56) References Cited

U.S. PATENT DOCUMENTS

| | | |
|---|---|---|
| 2012/0077717 A1 | 3/2012 | Musa et al. |
| 2013/0209376 A1 | 8/2013 | Prosise et al. |
| 2014/0224577 A1* | 8/2014 | Pathak ...................... B32B 7/12 181/290 |
| 2014/0296441 A1* | 10/2014 | Hood ...................... C08L 39/04 525/303 |

* cited by examiner

POLYMERS FOR ORAL CARE COMPOSITIONS

FIELD OF INVENTION

The present application provides water-soluble or water-dispersible polymers. The water-soluble or water-dispersible polymer comprises a first monomer having hydrogen bonding/complexing properties to polyphenols, a second monomer having detergent properties, and a third monomer having hydrogen bonding/complexing properties to polyphenols, wherein the first monomer and the third monomer are the same or different. The present invention also provides oral care compositions comprising the water-soluble or water-dispersible polymers. The present invention also provides methods of cleaning, whitening and polishing natural teeth and dental prosthesis and of preventing, reducing or removing surface deposited stains from teeth by administering the oral care compositions.

BACKGROUND OF THE INVENTION

Oral care compositions such as mouthwashes and toothpastes are generally designed to inhibit or kill microorganisms that cause gum disease, retard or stop plaque formation, prevent caries and to provide teeth whitening. Teeth whitening is typically done through the use of abrasive agents or bleaching agents. Factors that enlist teeth staining include the use of coffee, tea red wine, cola, tobacco products, or other stain promoting oral products. The disadvantage of using highly abrasive toothpastes, typically used in whitening toothpaste formulations, is the potential for the destruction of tooth enamel. Tooth bleaching agents, such as hydrogen peroxide, can be harsh to oral tissue and can often cause tooth sensitivity. This invention describes a gentle means of whitening teeth which is non-abrasive and non-oxidative in nature.

Water-soluble or water-dispersible copolymer, or water-soluble salts for oral care compositions are disclosed in U.S. Pat. No. 6,682,722 and WO1999/12517.

Hydroxyethylpyrrolidone methacrylate (M-06) and related compounds are disclosed in DE/2048312A1, U.S. Pat. No. 6,902,740B2, United States Patent publication No. 2013/0150481A1, European Patent No. EP2501728B1, W0/2014/160604A1, JP2011178863A, US/2009/0303304A1 and U.S. Pat. No. 3,067,163A.

Accordingly, it would be advantageous to have improved oral care compositions, without the need of high amount of abrasive agents or bleaching agents, to remove stains from teeth and whiten and polish teeth more effectively.

SUMMARY OF THE INVENTION

One of the objectives of present application is to provide water-soluble or water-dispersible polymers comprising a first monomer providing hydrogen bonding/complexing properties to polyphenols, a second monomer having detergent properties, and a third monomer having hydrogen bonding/complexing properties to polyphenols, wherein the first monomer and the third monomer are the same or different.

Another objective of the present application is to provide oral care compositions comprising the water-soluble or water-dispersible polymers. The present invention also provides methods of cleaning, whitening and polishing natural teeth and dental prosthesis and of preventing, reducing or removing surface deposited stains from teeth by administering the oral care compositions.

BRIEF DESCRIPTION OF THE DRAWINGS

The above objects and other features and advantages of the present invention will become more apparent by describing the preferred embodiment thereof with reference to the accompanying drawings, in which.

DETAILED DESCRIPTION OF THE INVENTION

Figure 1:
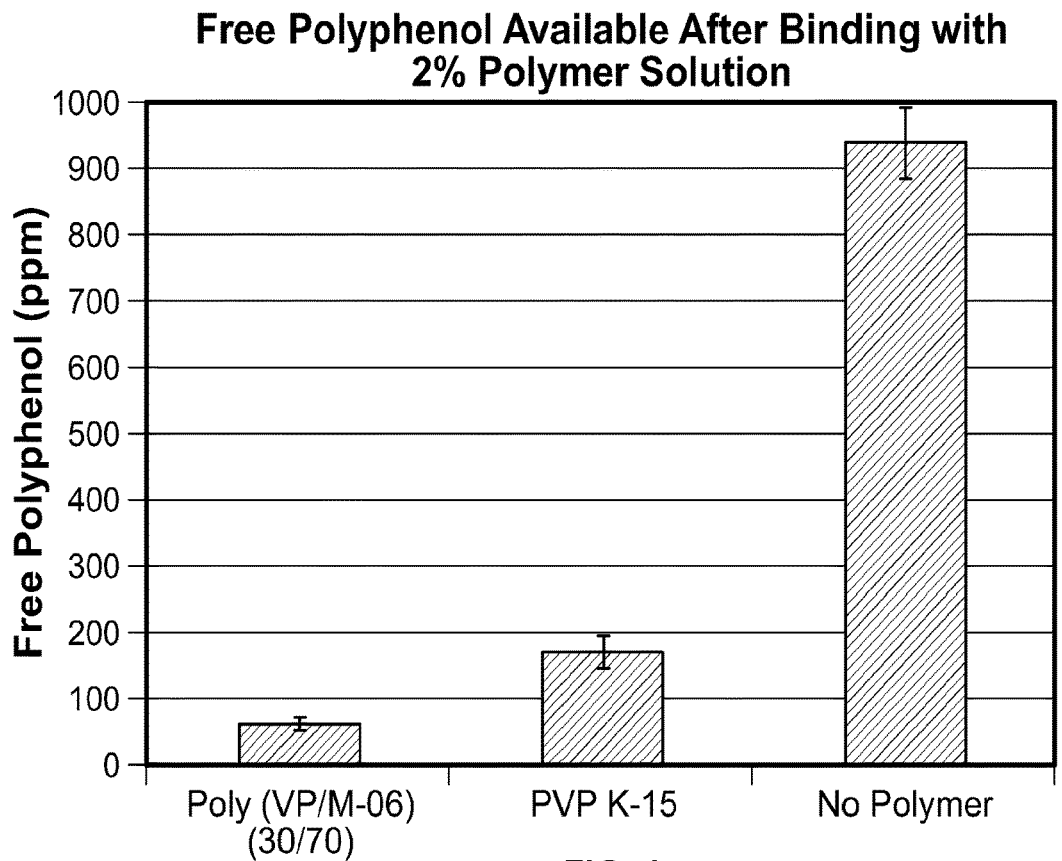
FIG. 1: Binding of a selected polyphenol staining agent to No Polymer, Polyvinylpyrrolidone, and Vinylpyrrolidone/Hydroxyethylpyrolidone Methacrylate.

The present invention provides oral care compositions for overall cleaning and whitening of natural teeth and dental prosthesis and for reducing, removing or preventing of stains on teeth. The present invention provides a water-soluble polymer comprising a first monomer having hydrogen bonding/complexing properties to polyphenols, a second monomer having detergent properties, and a third monomer having hydrogen bonding/complexing properties to polyphenols, wherein the first monomer and the third monomer are the same or different.

The present invention also provides methods of cleaning, whitening and polishing natural teeth and dental prosthesis and of reducing, removing or preventing stains from teeth by administering the oral care compositions.

As used herein, the following terms, unless otherwise indicated, have the meanings set out below.

The term "a" or "an" when used in conjunction with the term "comprising" may mean "on," but it is also consistent with the meaning of "one or more," "at least one," and "one or more than one." The use of the term "or" is used to mean "and/or" unless explicitly indicated to refer to alternatives only if the alternatives are mutually exclusive, although the disclosure supports a definition that refers to only alternatives and "and/or."

The term "about" refers to a value that includes the inherent variation of error for the quantifying device, the method being employed to determine the value, or the variation that exists among the study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent.

The term "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "or combinations thereof" as used herein refers to all permutations and combinations of the listed items preceding the term. For example, "A, $B_{Xn}$, $B_{Xn+1}$, or combinations thereof" is intended to include at least one of: A, $B_{Xn}$, $B_{Xn+1}$, $AB_{Xn}$, A $B_{Xn+1}$, $B_{Xn}B_{Xn+1}$, or $AB_{Xn}B_{Xn+1}$ and, if order is important in a particular context, also $B_{Xn}A$, $B_{Xn+1}A$, $B_{Xn+1}B_{Xn}$, $B_{Xn+1}B_{Xn}A$, $B_{Xn}B_{Xn+1}A$, $AB_{Xn+1}B_{Xn}$, $B_{Xn}AB_{Xn+1}$, or $B_{Xn+1}AB_{Xn}$. Continuing with this example, expressly included are combinations that contain repeats of one or more item or term, such as $B_{Xn}B_{Xn}$, AAA, $MB_{Xn}$, $B_{Xn}B_{Xn}B_{Xn+1}$, $AAAB_{Xn}B_{Xn+1}B_{Xn+1}B_{Xn+1}B_{Xn+1}$, $B_{Xn+1}B_{Xn}B_{Xn}$ AAA, $B_{Xn+1}AB_{Xn}AB_{Xn}B_{Xn}$, and so forth. The skilled artisan will understand that typically there is no limit on the number of items or terms in any combination, unless otherwise apparent from the context.

The term "at least one" refers to one as well as any quantity more than one, including but not limited to 1, 2, 3, 4, 5, 10, 15, 20, 30, 40, 50, 100, etc. The term "at least one" may extend up to 100 or 1000 or more depending on the term to which it is attached. In addition, the quantities of 100/1000 are not to be considered limiting as lower or higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first", "second", "third", "fourth", etc.) is solely for the purpose of differentiating between two or more items and, unless otherwise stated, is not meant to imply any sequence or order or importance to one item over another or any order of addition.

The term "pH" refers to a measure of the acidity or basicity of an aqueous solution. Pure water is considered to be neutral, with a pH close to 7.0 at 25°C. Solutions with a pH less than 7 are considered to be acidic and solutions with a pH greater than 7 are considered to be basic or alkaline.

The term "detergent" refers to a substance or preparation containing soaps and/or other surfactants intended for washing and cleaning processes. Thus detergents are cleansing agents that differ from soap but can also emulsify oils and hold dirt in suspension. Detergents may be in any form (liquid, powder, paste, bar, cake, moulded piece, shape, etc.) and used e.g., in personal care, household, or institutional or industrial purposes.

The term "copolymer" refers to chains comprising more than one type of monomer unit.

The term "polymer" refers to a large molecule comprising one or more types of monomer residues (repeating units) connected by covalent chemical bonds. By this definition, polymer encompasses compounds wherein the number of monomer units may range from very few, which more commonly may be called as oligomers, to very many. Non-limiting limiting examples of polymers include homopolymers, and non-homopolymers such as copolymers, terpolymers, tetrapolymers and the higher analogues. The polymer may have a random, block, and/or alternating architecture.

The term "homopolymer" refers to a polymer that consists essentially of a single monomer type.

The term "non-homopolymer" refers to a polymer formed from two or more monomers and includes essentially all polymers that are not homopolymers. Nonlimiting examples of non-homopolymers include copolymers, terpolymers, tetramers, and the like, wherein the non-homopolymer is a random, blocked, or alternating polymer.

The term "terpolymer" refers to a non-homopolymer that comprises three different monomer types.

The term "x, y or z" refers to integers commonly used in polymers and denote the molar percentage of each monomer in a polymer composition.

All percentages, ratios, and proportions used herein are based on a molar basis unless other specified.

The term "polymerization" refers to methods for chemically reacting monomer compounds to form polymer chains. The polymer chain may be alternating, branched, blocked, or random. The type of polymerization method may be selected from a wide variety of methods. Such methods include, but are not limited to; free radical polymerization methods, such as classical radical polymerization and controlled radical polymerization, Nitroxide Mediation Polymerization (NMP), Atom Transfer Radical Polymerization (ATRP), and Reversible Addition Fragmentation Chain-Transfer (RAFT).

The term "hydrogen bond" or "hydrogen bonding" refers to an electrostatic attraction between an electropositive hydrogen atom (covalently bound to a highly electronegative atom such as nitrogen or oxygen) and another highly electronegative atom in close proximity. It is not a chemical union and has lower free energies than those of a covalent or ionic bond.

In the context of this application, the term "complexing" refers to an association between two molecules (e.g. electrostatic or other interactions).

The term "monomer" refers to the repeat units comprising a polymer. A monomer is a small molecule that chemically bonds to other monomers to form a polymer.

The term "M-06" refers to N-(2-hydroxyethyl)pyrrolidone methacrylate/hydroxyethylpyrolidone methacrylate, having a structure of

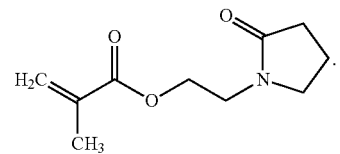

The term "acryloyl" refers to a moiety having the generic structure:

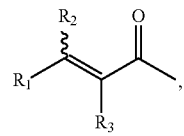

wherein each R1, R2 and R3 is independently selected from the group consisting of hydrogen and functionalized and unfunctionalized alkyl, alkenyl, aryl, nitrile, formyl, carboxyl, carboxylate salt, carboxylic ester, carboxamide, halogen, thiocarboxylate, and combinations thereof.

The term "alkyl" refers to a functionalized or unfunctionalized monovalent straight-chain, branched-chain or cyclic C1-C60 group optionally having one or more heteroatoms. Particularly, an alkyl is a C1-C45 group and more particularly, a C1-C30 group. Particular, yet non-limiting examples of alkyl groups include methyl, ethyl, n-propyl, isopropyl, n-butyl, isobutyl, tert-butyl, cyclobutyl, n-pentyl, isopentyl, cyclopentyl, n-hexyl, cyclohexyl, n-heptyl, cyclyheptyl, methylcyclohexyl, n-octyl, 2-ethylhexyl, tert-octyl, iso-norbornyl, n-dodecyl, tert-docdecyl, n-tetradecyl, n-hexadecyl, n-octadecyl, and n-eicosyl.

The term "alkyl (alk) acrylate" refers to an alkyl ester of an acrylic acid or an alkyl acrylic acid.

The term "alkyl (alk) acrylamide" refers to an alkyl amide of an acrylic acid or an alkyl acrylic acid.

The term "alkylene" refers to a functionalized or unfunctionalized divalent straight-chain, branched-chain or cyclic C1-C40 group optionally having one or more heteroatoms. Particularly, an alkylene is a C1-C45 group and more particularly, a C1-C30 group. Particularly, yet non-limiting examples of alkylene groups include —CH2—, —CH2—CH2—, —CH(CH3)—CH2—, —CH2—CH(CH3)—, —C(CH3)2—CH2—, —CH2—C(CH3)2—, —CH(CH3)—CH(CH3)—, —C(CH3)2—C(CH3)2—, —CH2—CH2—CH2—, —CH(CH3)—CH2—CH2—, —CH2—CH(CH3)—CH2—, —CH2—CH2—CH(CH3)—, —CH2—CH2—CH2—CH2—, —CH2—CH2—CH2—CH2—CH2—, —CH2—CH2—CH2—CH2—CH2—CH2—, —CH2—CH2—CH2—CH2—CH2—CH2—CH2—, cyclopropylene, cyclobutylene, cyclopentylene, cyclohexylene, and the like.

The term "ammonium" refers to protonated NH3 and protonated primary, secondary, and tertiary organic amines.

The term "metal ion" refers to alkali metal ions, alkaline earth metal ions, and transition metal ions. For example, sodium, calcium, copper and iron derived ions.

The term "mineral acid" refers to an acid derived from one or more inorganic compounds. Mineral acids release hydrogen ions when dissolved in water. Commonly used mineral acids are sulfuric acid, hydrochloric acid, and nitric acid.

The term "branched and unbranched alkyl groups" refers to alkyl groups, which may be straight chained or branched. For example, the alkyl groups have from 1 to about 18 carbon atoms, more particularly, from 1 to about 10 carbon atoms, and yet more particularly from 1 to about 6 carbon atoms. Branched groups include isopropyl, tert-butyl, and the like.

The term "leaving group" refers to any group that can be displaced by an azide ion. Nonlimiting examples include halogens, silyl groups, tosyl groups, and mesyl groups.

The term "ligation" refers to an act of uniting or connecting two or more starting materials or reactants.

The term "each independently selected from the group consisting of" refers to a group appears more than once in a structure, that group may be selected independently each time it appears.

The term "free radical addition polymerization initiator" refers to a compound used in a catalytic amount to initiate a free radical addition polymerization. The choice of initiator depends mainly upon its solubility and its decomposition temperature.

The term "functionalized" refers to the state of a moiety that has one or more functional groups introduced to it by way of one or more functionalization reactions known to a person having ordinary skill in the art. Particular, yet non-limiting examples of functionalization reactions include epoxidation, sulfonation, hydrolysis, amidation, esterification, hydroxylation, dihyroxylation, amination, ammonolysis, acylation, nitration, oxidation, dehydration, elimination, hydration, dehydrogenation, hydrogenation, acetalization, halogenation, dehydrohalogenation, Michael addition, aldol condensation, Canizzaro reaction, Mannich reaction, Clasien condensation, Suzuki coupling, and the like. Particularly, functionalization of a moiety replaces one or more hydrogens in the moiety with one or more non-hydrogen groups, for e.g., alkyl, alkoxyl, cycloalkyl, alkenyl, cycloalkenyl, alkynyl, and/or aryl groups. Particular, yet non-limiting examples of cycloalkyl groups include cyclopentane, cyclohexane, cycloheptane, and the like. Particular, yet non-limiting examples of alkoxy groups include methoxy, ethoxy, n-propoxy, isopropoxy, and the like. Particular, yet non-limiting examples of aryl groups include benzenes, naphthalenes (2 rings), anthracenes (3 rings), and the like.

The term "halogen" refers to chloro, bromo, iodo and fluoro, and in one embodiment is bromo and/or chloro.

The term "heteroatom" refers to atoms such as oxygen, nitrogen, sulfur, silicon, phosphorous, and/or halogen. The heteroatom(s) may be present as a part of one or more heteroatom-containing functional groups and/or as a part of one or more heterocyclic rings. Non-limiting examples of heteroatom-containing functional groups include ether, hydroxy, epoxy, carbonyl, carboxamide, carboxylic ester, carboxylic acid, imine, imide, amine, sulfonic, sulfonamide, phosphonic, and silane groups.

The term "hydrocarbyl" refers to a straight-chain and branched-chain alkyl, alkenyl, alkynyl, cycloalkyl, cycloalkenyl, aryl groups, and combinations thereof with optional heteroatom(s). A hydrocarbyl group may be mono-, di- or polyvalent.

The term "organic moiety" refers to an unsubstituted or substituted alkyl, cycloalkyl, alkenyl, and aryl groups, wherein any of the before mentioned groups may be present with or without heteroatoms. The alkyl and alkenyl groups may be branched or unbranched (straight-chain). Preferably, the alkyl and alkenyl groups are C1-C60, more preferably C1-C36, and most preferably C1-C18 groups. Cycloalkyls (closed rings) include cyclopentane, cyclohexane, cycloheptane; and the like. Aryl groups include benzenes, naphthalenes (2 rings), and anthracenes (3 rings), and the like.

The term "polyphosphate" refers to a group having two or more phosphate groups arranged primarily in a linear configuration, although some cyclic derivatives may be present.

The term "non-aqueous" refers to a state of not being aqueous in nature. By "non -aqueous" it is generally meant that water is not deliberately added to the composition in any significant quantity. However, the term "non-aqueous" does not mean that small amounts of water cannot be present, for example as a consequence of its association with hygroscopic raw materials. Accordingly, for the purposes of this invention, the term "non-aqueous" generally refers to that water is present in an amount no greater than about 5%, more preferably no greater than about 3% by weight based on the total weight of the composition.

The term "dentifrice" refers to pastes, gels, or liquid formulations unless otherwise specified. The dentifrice composition may be a single-phase composition or may be a combination of two or more dentifrice compositions. The dentifrice composition may be in any desired form, such as deep striped, surface striped, multilayered, having the gel surrounding the paste, or any combinations thereof. Each dentifrice composition in a dentifrice comprising two or more separate dentifrice compositions may be contained in a physically separated compartment of a dispenser and dispensed side-by-side.

The term "lozenge" refers to breath mints, troches, pastilles, microcapsules, and fast-dissolving solid forms including freeze dried forms (cakes, wafers, thin films, tablets) and fast-dissolving solid forms including compressed tablets.

The term "oral composition" refers to a product which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral composition of the present invention may be in the form of a toothpaste, dentifrice, tooth powder, topical oral gel, mouth rinse, denture product, mouth spray, lozenge, oral tablet, or chewing gum.

The term "orally acceptable carrier" refers to any safe and effective materials for use in the compositions of the present invention. Such materials include fluoride ion sources, additional anticalculus agents, buffers, abrasive polishing materials, peroxide sources, alkali metal bicarbonate salts, thickening materials, humectants, water, surfactants, titanium dioxide, flavor system, sweetening agents, xylitol, coloring agents, and mixtures thereof.

The term "pharmaceutically active ingredient" refers to any ingredient considered to have a therapeutic effect when delivered to a subject in need thereof and further being regulated by drug authorities like CDER, EMEA, TAG etc. Pharmaceutically active ingredients may act systemically upon oral consumption, or locally such as when present in the buccal cavity, on the skin, etc. They may also be delivered across the skin as in transdermal drug delivery systems.

The terms "pharmaceutically acceptable" or "cosmetically acceptable" refers to molecular entities and compositions that are generally regarded as safe. Particularly; as used herein, the term "pharmaceutically acceptable" or "cosmetically acceptable" refers to approved by a regulatory agency of the appropriate governmental agency or listed in the U.S. Pharmacopoeia or other generally recognized pharmacopoeia for use in animals, and more particularly in humans.

The terms "tartar" and "calculus" are used interchangeably and refer to mineralized dental plaque deposits.

The term "teeth" refers to natural teeth as well as artificial teeth or dental prosthesis.

The term "dispenser" refers to any pump, tube, or container suitable for dispensing toothpaste.

The present invention provides a water-soluble or water-dispersible polymers for removing stains from teeth. The water-soluble or water-dispersible polymer comprise a first monomer having hydrogen bonding/complexing properties to polyphenols, a second monomer having detergent properties, and a third monomer having hydrogen bonding/complexing properties to polyphenols, wherein the first monomer and the third monomer are the same or different.

The present invention also provides oral compositions comprising the water-soluble or water-dispersible polymers. The oral care compositions provide enhanced overall cleaning, whitening and stain removal from teeth:

The first monomer having hydrogen bonding/complexing properties to polyphenols may be selected from the group consisting of vinyl pyrrolidone, hydroxyethylpyrrolidone methacrylate, vinyl caprolactam, vinyl acetate, vinyl imidazole, poly(ethylene glycol) methyl ether methacrylate, and poly(ethylene glycol) methacrylate. Preferably, the first monomer is vinyl pyrrolidone or hydroxyethylpyrrolidone methacrylate (M-06).

In particular embodiments, the first monomer having hydrogen bonding/complexing properties has at least one functionalized or unfuntionalized acryloyl moiety and at least one lactam moiety. Non-limiting examples of the first monomer may be selected from the group consisting of:

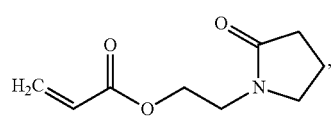

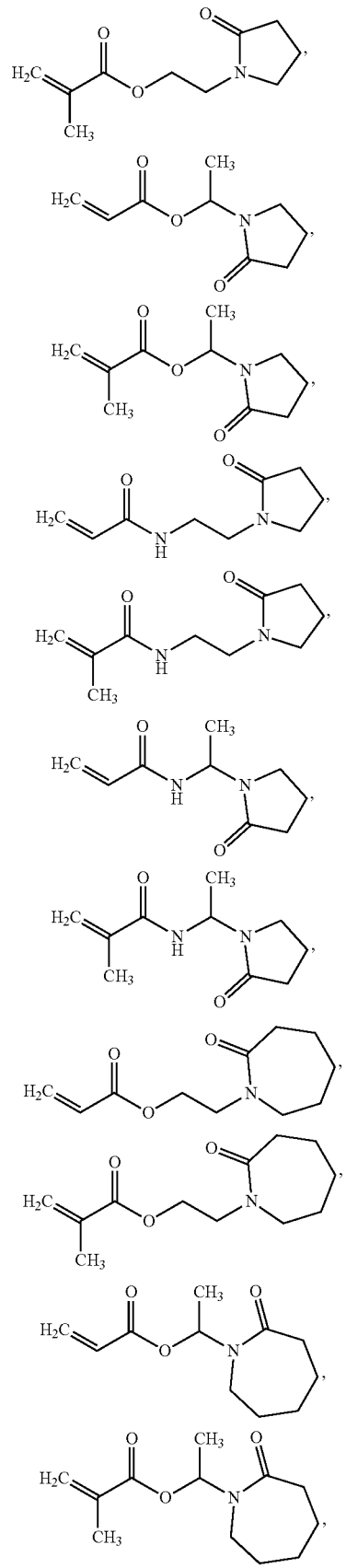

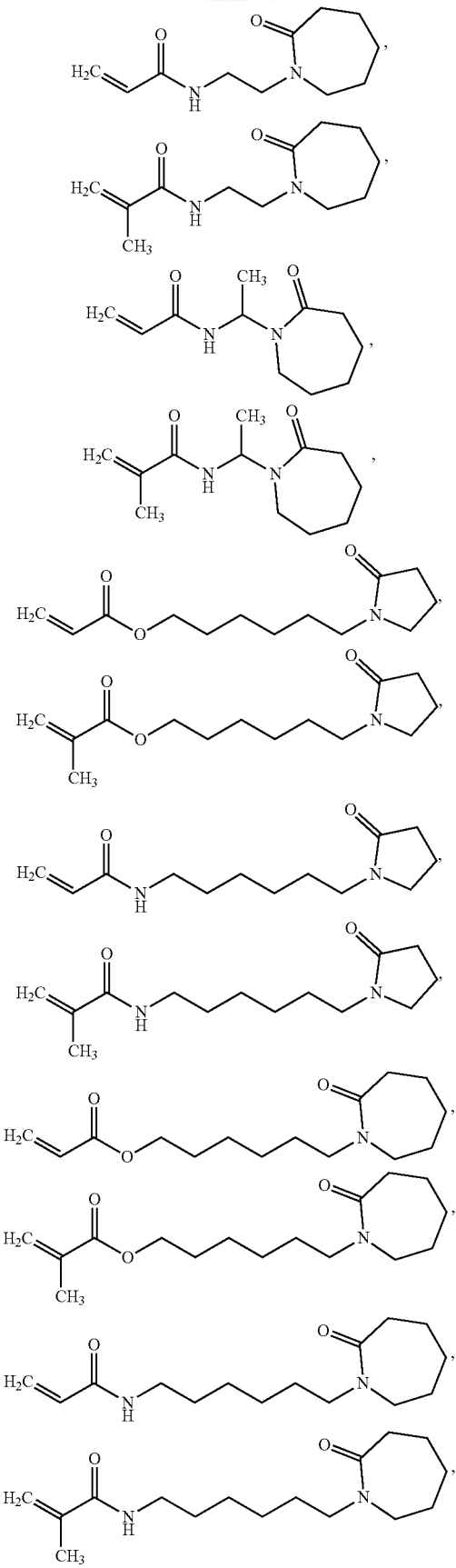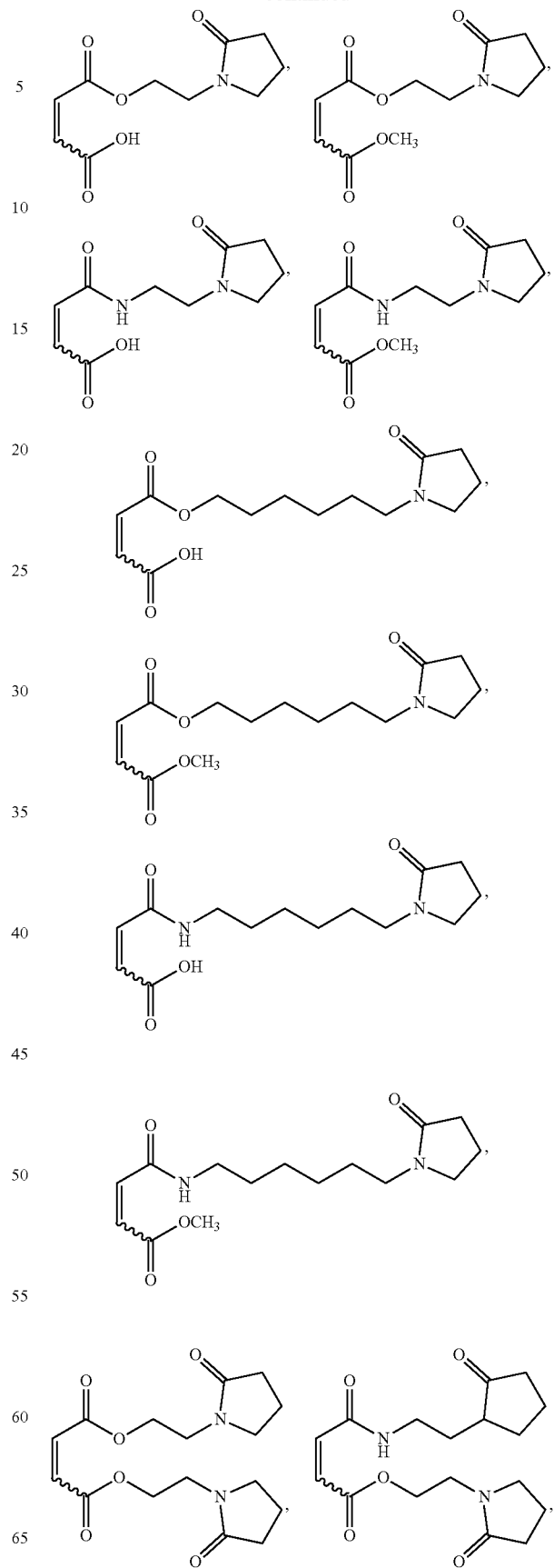

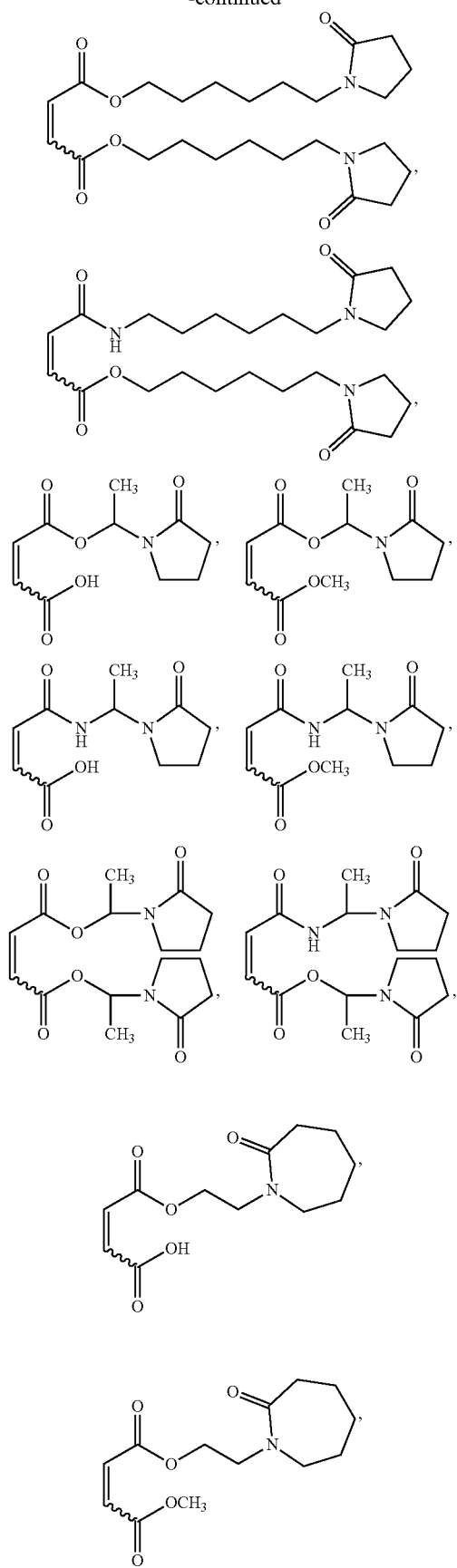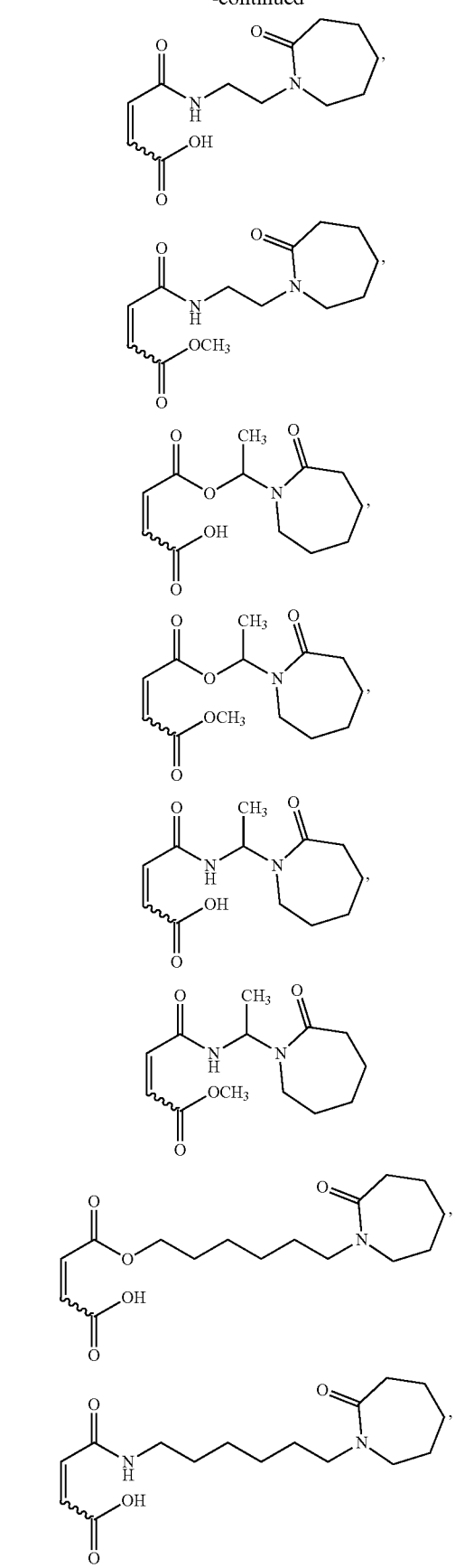

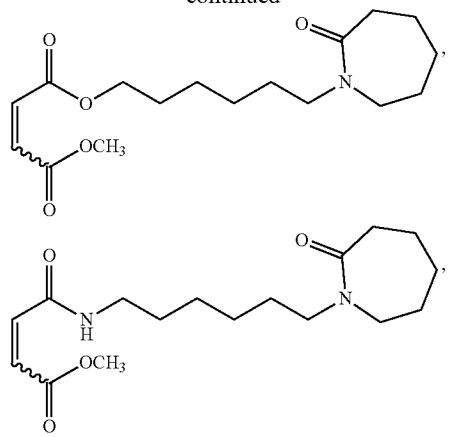

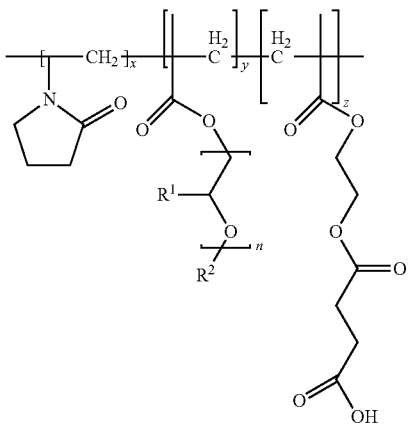

wherein x=5-90, y=5-90, z=5-90, mole %, and n is an integer ranging from 1 to about 100, and, $R^1$, $R^2$=H or $CH_3$,

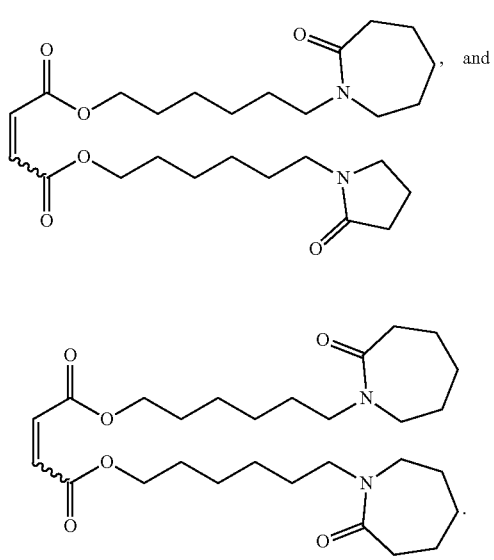

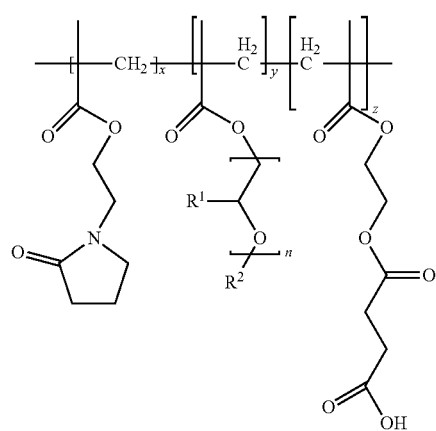

Other suitable examples can be found in WO 2011/063208, the disclosure of which is incorporated herein by reference in its entirety.

In accordance with certain aspects, the second monomer provides detergent properties. Non-limiting examples of the second monomer may be selected from the group consisting of poly(ethylene glycol) methyl ether methacrylate, poly(ethylene glycol) methacrylate, poly(propylene glycol) methyl ether methacrylate, poly(propylene glycol) methacrylate, 2-acrylamido-2-methylpropane sulfonic acid, hydroxypolyethoxy allyl ether, 3-sulfopropyl methacrylate, vinylsulfonic acid/sodium salt, and 1-allyloxy-2 hydroxypropyl sulfonate/sodium salt. According to one of the embodiment, the second class of monomers or copolymers is poly(ethylene glycol) methyl ether methacrylate.

The third monomer provides hydrogen bonding/complexing properties to polyphenols. According to one embodiment, the third monomer is mono-2-(methacryloyloxy) ethyl succinate or acetoacetoxyethyl methacrylate.

The structure of the water-soluble or water-dispersible may be selected from the group consisting of:

wherein x=5-90, y=5-90, z=5-90, mole %, and n is an integer ranging from 1 to about 100, and, $R^1$, $R^2$=H or $CH_3$,

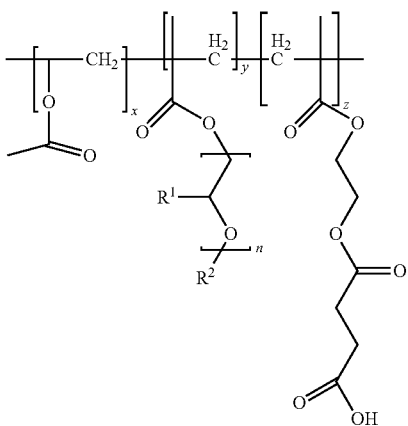

wherein x=5-90, y=5-90, z=5-90, mole %, and n is an integer ranging from 1 to about 100, and, $R^1$, $R^2$=H or $CH_3$,

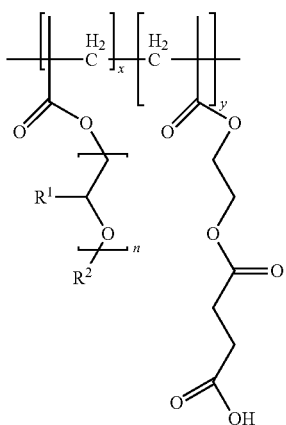

wherein x=5-95, y=5-95, mole %, and n is an integer ranging from 1 to about 100, and, $R^1$, $R^2$=H or CH$_3$,

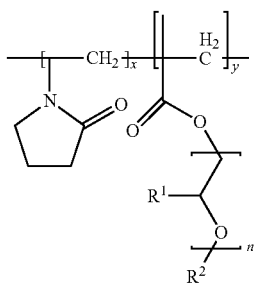

wherein x=5-95, y=5-95, mole %, and n is an integer ranging from 1 to about 100, and, $R^1$, $R^2$=H or CH$_3$, and,

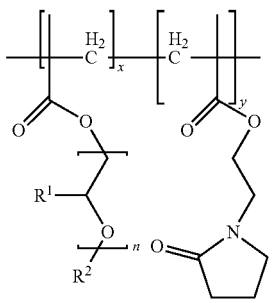

wherein x=5-95, y=5-95, mole %, and n is an integer ranging from 1 to about 100, and, $R^1$, $R^2$=H or CH$_3$.

Preferably, the structure of the water-soluble or water-dispersible polymer can be selected from the group consisting of:

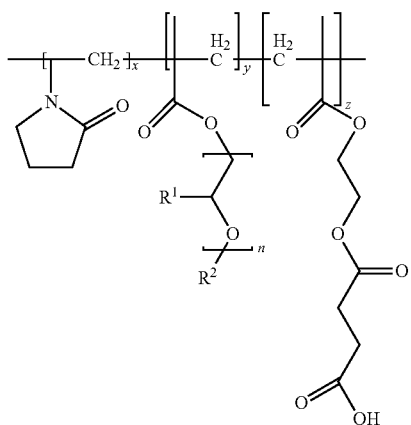

wherein x=5-90, y=5-90, z=5-90, mole %, and n is an integer ranging from 1 to about 100, and, $R^1$, $R^2$=H or CH$_3$,

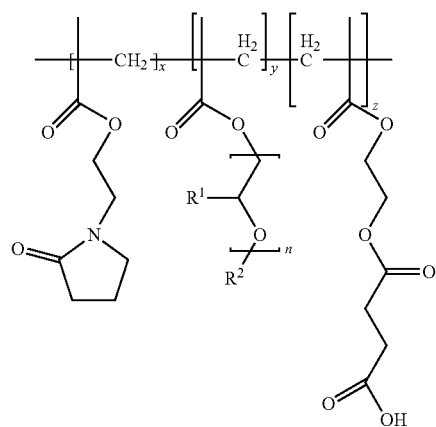

wherein x=5-90, y=5-90, z=5-90, mole %, and n is an integer ranging from 1 to about 100, and, $R^1$, $R^2$=H or CH$_3$, and

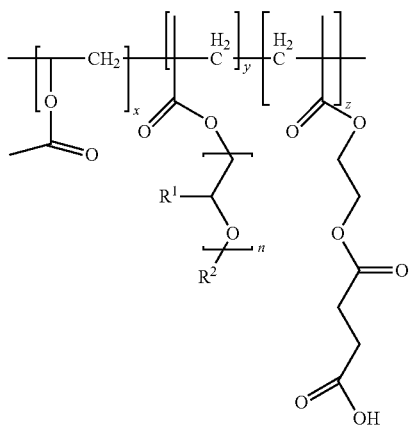

wherein x=5-90, y=5-90, z=5-90, mole %, and n is an integer ranging from 1 to about 100, and, $R^1$, $R^2$=H or CH$_3$.

According to one embodiment of the invention, the structure of the water-soluble or water-dispersible polymer can be selected from the group consisting of:

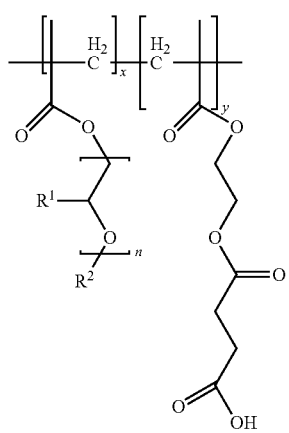

wherein x=5-95, y=5-95, mole %, and n is an integer ranging from 1 to about 100, and, $R^1$, $R^2$=H or $CH_3$,

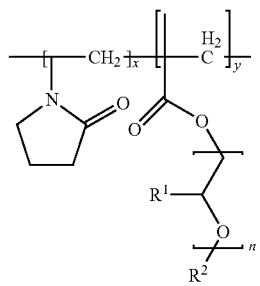

wherein x=5-95, y=5-95, mole %, and n is an integer ranging from 1 to about 100, and, $R^1$, $R^2$=H or $CH_3$, and

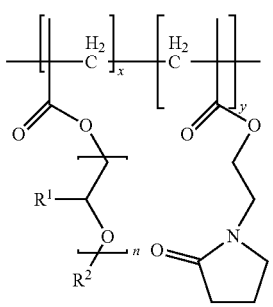

wherein x=5-95, y=5-95, mole %, and n is an integer ranging from 1 to about 100, and, $R^1$, $R^2$=H or $CH_3$.

According to another embodiment of the invention, the structure of the water-soluble or water-dispersible polymer can be selected from the group consisting of:

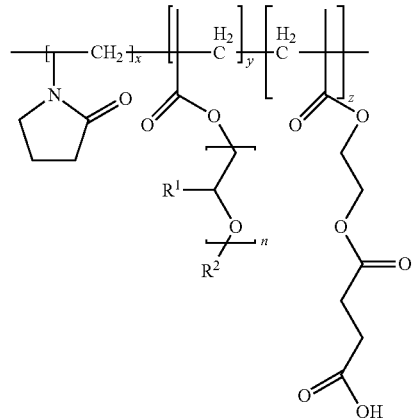

wherein x=5-90, y=5-90, z=5-90, mole %, and n is an integer ranging from 1 to about 100, and, $R^1$, $R^2$=H or $CH_3$, or

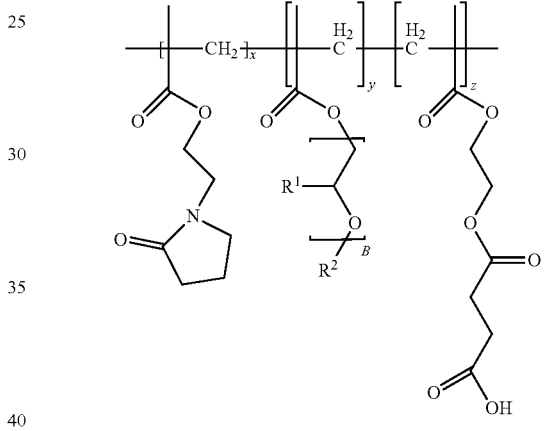

wherein x=5-90, y=5-90, z=5-90, mole %, and n is an integer ranging from 1 to about 100, and, $R^1$, $R^2$=H or $CH_3$.

Preferably, the structure of the water-soluble or water-dispersible polymer is:

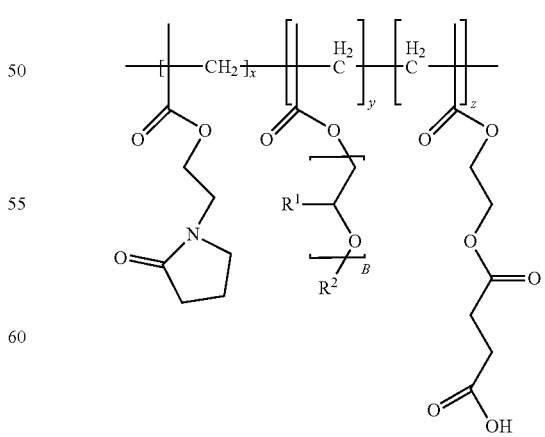

wherein x=5-90, y=5-90, z=5-90, mole %, and n is an integer ranging from 1 to about 100, and, $R^1$, $R^2$=H or $CH_3$.

The water-soluble or water-dispersible polymer structure can be random, block, or grafted. Preferred water-soluble or water-dispersible polymers have an average molecular weight ranging from about 1,000 to about 1,000,000 Daltons, preferably from about 10,000 to 200,000, even more preferably from about 10,000 to 100,000.

The present invention also provides an oral care composition comprising: (a) an oral care acceptable carrier, and (b) at least about 0.1% by weight of a water-soluble or water dispersible polymer comprising a first monomer having hydrogen bonding/complexing properties to polyphenols, a second monomer having detergent properties, and a third monomer having hydrogen bonding/complexing properties to polyphenols, wherein the first monomer and the third monomer are the same or different, wherein the oral care acceptable carrier is a toothpaste, dentifrice, tooth powder, topical oral gel, mouth rinse, denture product, mouth spray, lozenge, oral tablet, chewing gum, fast-dissolving films, strips, or impregnated dental implement, wherein the composition provides stain removal from teeth. An orally acceptable carrier comprises one or more compatible solid or liquid filler diluents or encapsulating substances which are suitable for topical oral administration. The term compatible, as used herein, is meant that the components of the composition are capable of being commingled without interaction in a manner which would substantially reduce the composition's stability and/or efficacy.

The choice of orally acceptable carder to be used is determined by the way the composition is to be introduced into the oral cavity. If a toothpaste, including tooth gels, other dentifrices, etc. is to be used, then a toothpaste carrier is chosen (e.g., abrasive materials, foaming agents, binders, humectants, flavoring and sweetening agents. If a mouth rinse is to be used, then a mouth rinse carrier is chosen. Similarly, if a mouth spray is to be used, then a mouth spray carrier is chosen or if a lozenge is to be used, then a lozenge carrier is chosen (e.g., a candy base). If a chewing gum is to be used, then a chewing gum carrier is chosen. If a sachet is to be used, then a sachet carrier is chosen, sachet bag, flavoring, and sweetening agents. If a subgingival gel is to be used, for delivery of actives into the periodontal pockets or around the periodontal pockets, then a subgingival gel carrier is chosen. Carriers suitable for the preparation of compositions of the present invention are well known in the art. Their selection will depend on secondary considerations like taste, cost, and shelf stability, etc.

The orally acceptable carriers or excipients of the present invention can include the usual components of dentifrices (including non-abrasive gels and gels for subginaival application), mouth rinses, mouth sprays, chewing gums, and lozenges (including breath mints).

The oral care compositions further comprise about 20% of a polishing agent or abrasive, preferably a silica abrasive, by weight.

The oral care compositions can also comprise a chelating agent such as tartaric acid and pharmaceutically acceptable salts thereof, citric acid and alkali metal citrates and mixtures thereof. Chelating agents are able to complex calcium found in the cell walls of the bacteria. Chelating agents can also disrupt plaque by removing calcium from the calcium bridges which help hold this biomass intact. However, it is not desired to use a chelating agent which has an affinity for calcium that is too high, as this may result in tooth demineralization, which is contrary to the objects and intentions of the present invention. Sodium and potassium citrate are the preferred alkali metal citrates, with sodium citrate being the most preferred. Also preferred is a citric acid/alkali metal citrate combination. Preferred herein are alkali metal salts of tartaric acid. Most preferred for use herein are disodium tartrate, dipotassium tartrate, sodium potassium tartrate, sodium hydrogen tartrate and potassium hydrogen tartrate. The amounts of chelating agent suitable for use in the present invention are about 0.1% to about 2.5%, preferably from about 0.5% to about 2.5% and more preferably from about 1.0% to about 2.5%. The tartaric acid salt chelating agent can be used alone or in combination with other optional chelating agents. Other optional chelating agents can be used.

Other chelating agents suitable for use are the anionic polymeric polycarboxylates in the form of their free acids or partially or preferably fully neutralized water-soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (methoxyethylene) having a molecular weight of about 30,000 to about 1,500,000.

The oral care compositions comprising the water-soluble or water-dispersible polymers may further comprise about 3% by weight of a water-soluble polyphosphate salt and/or about 20% by weight of an abrasive polishing agent, such as silica, and/or about 0.1% of a bleaching agent.

The oral care compositions may further comprise a water-soluble alkali metal or ammonium polyphosphate salt in an amount in the range of about 0:5% to about 50%, by weight.

The oral care compositions may further comprise a teeth whitening agent, such as a bleach such as a peroxide.

The oral care compositions may also comprise an additional water-soluble fluoride compound present in dentifrices and other oral compositions in an amount sufficient to give a fluoride ion concentration in the composition at 25° C., and/or when it is used of from about 0.0025% to about 5.0% by weight, preferably from about 0.005% to about 2.0% by weight, to provide additional anticaries effectiveness. A wide variety of fluoride ion-yielding materials can be employed as sources of soluble fluoride in the present compositions. Representative fluoride ion sources include: stannous fluoride, sodium fluoride, potassium fluoride, sodium monofluorophosphate and many others. Stannous fluoride and sodium fluoride are particularly preferred, as well as mixtures thereof.

The oral care compositions may further comprise surfactants which are reasonably stable and foam throughout a wide pH range. The surfactant can be anionic, nonionic, amphoteric, zwitterionic, cationic, or mixtures thereof.

The anionic surfactants include water-soluble salts of alkyl sulfates having from 8 to 20 carbon atoms in the alkyl radical (e.g. sodium alkyl sulfate) and the water-soluble salts of sulfonated monoglycerides of fatty acids having from 8 to 20 carbon atoms, such as sodium lauryl sulfate and sodium coconut monoglyceride sulfonate. Other suitable anionic surfactants are sarcosinates, such as sodium lauryl sarcosinate, taurates, sodium lauryl sulfoacetate, sodium lauroyl isethionate, sodium lauryl carboxylate, and sodium dodecyl benzenesulfonate, and mixtures thereof. The oral care compositions further comprise an anionic surfactant in an amount from about 0.025% to about 9%, preferably from about 0.05% to about 5%, and most preferably from about 0.2% to about 3%.

Another preferred surfactant is selected from the group consisting of sarcosinate surfactants, isethionate surfactants and taurate surfactants. Preferred surfactants are alkali metal or ammonium salts of these surfactants and most preferred are the sodium and potassium salts of lauroyl sarcosinate, myristoyl sarcosinate, palmitoyl sarcosinate, stearyl sarcosinate, and oleoyl sarcosinate. These surfactants can be present in the oral care compositions in an amount from about 0.1% to about 2.5%, preferably from about 0.3% to about 2.5%, and most preferably from about 0.5% to about 2.0% by weight of the total composition.

Preferred cationic surfactants are derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc. Certain cationic surfactants can also act as germicides.

Preferred nonionic surfactants useful in the oral care compositions are compounds produced by the condensation of alkylene oxide groups (hydrophilic in nature) with an organic hydrophobic compound which can be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Preferred zwitterionic are derivatives of aliphatic quaternary ammonium; phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

The oral care compositions further comprise surfactants including but not limited to alkyl dimethyl betaines. The alkyl dimethyl betaines include decyl betaine or 2-(N-decyl-N,N-dimethylammonio)acetate, coco betaine or 2-(N-coc-N,N-dimethyl ammonio) acetate, myristyl betaine, palmityl betaine, lauryl betaine, cetyl betaine, cetyl betaine, stearyl betaine, etc. The amido-betaines are exemplified by cocoamidoethyl betaine, cocoamidopropyl betaine, lauramidopropyl betaine and the like. Preferably, the betaines are cocoamidopropyl betaine, and more preferably, lauramidopropyl betaine.

The oral care compositions may further comprise antibacterial agents including but not limited to halogenated diphenyl ether, 2,4,4'-trichloro-2'-hydroxy-diphenyl ether, 2,2'-dihydroxy-5,5'-dibromo-diphenyl ether, 2,2'-methylenebis-4(4-chloro-6-bromo-phenol), halogenated salicylanilides and halogenated cabanilides.

The oral care compositions may further comprise desensitizing agent including but not limited to potassium salt, capaicin, eugenol, a strontium salt, and combinations thereof.

The oral care compositions may further comprise an anticalculus agent, preferably a pyrophosphate ion source which is from a pyrophosphate salt. The pyrophosphate salts useful in the oral care compositions include the dialkali metal pyrophosphate salts, tetraalkali metal pyrophosphate salts, and mixtures thereof. Disodium dihydrogen pyrophosphate (Na2H2P2O7), tetrasodium pyrophosphate (Na4P2O7), and tetrapotassium pyrophosphate (K4P2O7) in their un-hydrated as well as hydrated forms are the preferred species. In the oral care compositions, the pyrophosphate salt can be present in the form of predominately dissolved, predominately undissolved, or a mixture of dissolved and undissolved pyrophosphate.

Optional agents in oral care composition include synthetic anionic polymers, including polyacrylates and copolymers of maleic anhydride or acid and methyl vinyl ether, polyamino propane sulfonic acid, zinc citrate trihydrate, polyphosphates, diphosphonates, polypeptides (such as polyaspartic and polyglutamic acids), and mixtures thereof.

Polyphosphates, including tripolyphosphates, tetrapolyphosphates, and hexametaphosphates, can also be included in the oral care compositions.

The oral care compositions may further comprise teeth whitening actives. The actives suitable for whitening include the peroxides, metal chlorites, perborates, percarbonates, peroxyacids, persulfates, and combinations thereof. Suitable peroxide compounds include hydrogen peroxide, urea peroxide, calcium peroxide, and mixtures thereof. Suitable metal chlorites include calcium chlorite, barium chlorite, magnesium chlorite, lithium chlorite, sodium chlorite, and potassium chlorite. The preferred chlorite is sodium chlorite. Additional whitening actives may be hypochlorite and chlorine dioxide. A preferred percarbonate is sodium percarbonate. Other suitable whitening agents include potassium, ammonium, sodium and lithium persulfates and perborate mono- and tetrahydrates, and sodium pyrophosphate peroxyhydrate.

The oral care compositions may further comprise thickening agents in toothpaste or gels. Preferred thickening agents are water-soluble cellulose ethers such as sodium carboxymethylcellulose, sodium carboxymethyl hydroxyethyl cellulose and, hydroxyethyl cellulose. Other suitable thickening agents include; carboxyvinyl polymers, carrageenan, laponite and other natural gums such as gum karaya, xanthan gum, guar gum, gum arabic, and gum tragacanth. Colloidal magnesium aluminum silicate or finely divided silica can be used as part of the thickening agent to further improve texture. A preferred class of thickening or gelling agents includes a class of homopolymers of acrylic acid cross-linked with an alkyl ether of pentaerythritol or an alkyl ether of sucrose, or carbomers.

The oral care compositions may further comprise copolymers of lactide and glycolide monomers, the copolymer having the molecular weight in the range of from about 1,000 to about 120,000 (number average), are useful for delivery of actives into the periodontal pockets or around the periodontal pockets as a subgingival gel carrier.

The thickening agents are present in an amount from about 0.1% to about 15%, preferably from about 0.2. to about 5.0%, more preferably from about 0.5% to about 2.0%, by weight of the total toothpaste or gel composition, can be used. Higher concentrations can be used for chewing gums, lozenges (including breath mints), sachets, non-abrasive gels and subgingival gels.

The oral care compositions may further comprise humectants. Humectants serve to keep toothpaste compositions from hardening upon exposure to air, to give compositions a moist feel to be mouth, and, for particular humectants, to impart desirable sweetness of flavor to toothpaste compositions. The humectant, on a pure humectant basis, generally comprises from about 0% to about 70%, preferably from about 20% to about 50%, by weight of the compositions herein. Suitable humectants for use in the oral care compositions include edible polyhydric alcohols such as glycerin, sorbitol, xylitol, butylene glycol, polyethylene glycol, and propylene glycol, especially sorbitol, and glycerin.

The oral care compositions may further comprise flavoring and sweetening agents. Flavoring aunts can also be added to the compositions. Suitable flavoring agents include wintergreen oil, peppermint oil, spearmint oil, clove bud oil, menthol, anethole, methyl salicylate, eucalyptol, cassia, 1-menthyl acetate, sage, eugenol, parsley oil, oxanone, alpha-insane, marjoram, lemon, orange, propenyl guaethol, cinnamon, vanillin, thymol, linalool, cinnamaldehyde glycerol acetal known as CGA, and mixtures thereof. Flavoring agents are generally used in the compositions at levels of from about 0.001% to about 5%, by weight of the composition.

The sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame, sucralose and cyclamate salts, especially sodium cyclamate and sodium saccharin, and mixtures thereof. A composition preferably contains from about 0.1% to about 10% of these agents, preferably from about 0.1% to about 1%, by weight of the composition.

In addition to flavoring and sweetening agents, coolants, salivating agents, warming agents, and numbing agents can be used as optional ingredients in compositions of the present invention. These agents are present in the compositions at a level of from about 0.001% to about 10%, preferably from about 0.1% to about 1%, by weight of the composition.

The coolant can be any of a wide variety of materials such as carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat.RTM. manufactured by Haarmann and Reimer. The terms menthol and menthyl as used herein include dextro- and levorotatory isomers of these compounds and racemic mixtures thereof.

The oral care compositions may further include an alkali metal bicarbonate salt. Alkali metal bicarbonate salts are soluble in water and unless stabilized, tent to release carbon dioxide in an aqueous system. Sodium bicarbonate, also known as baking soda, is the preferred alkali metal bicarbonate salt. The present composition may contain from about 0.5% to about 30%, preferably from about 0.5% to about 15%, and most preferably from about 0.5% to about 5% of an alkali metal bicarbonate salt.

Water employed in the preparation of commercially suitable oral compositions should preferably be of low ion content and free of organic impurities. Water generally comprises from about 5% to about 70%, and preferably from about 20% to about 50%, by weight of the aqueous compositions herein. These amounts of water include the free water which is added plus that which is introduced with other materials, such as with sorbitol.

Titanium dioxide can also be added to the present composition. Titanium dioxide is a white powder which adds opacity to the compositions. Titanium dioxide generally comprises from about 0.25% to about 5% by weight of the dentifrice compositions.

The pH of the present compositions is preferably adjusted through the use of buffering agents. Buffering agents, as used herein, refer to agents that can be used to adjust the pH of the compositions to a range of about pH 4.0 to about pH 10.0. Buffering agents include monosodium phosphate, trisodium phosphate, sodium hydroxide, sodium carbonate, sodium acid pyrophosphate, citric acid, and sodium citrate. Buffering agents can be administered at a level of from about 0.5% to about 10%, by weight of the present compositions.

The oral care compositions will optimally have a pH ranging from about 4.0 to about 10.0. Preferred pH of the compositions is from about 6.0 to about 9.0.

The oral care compositions can be in the form of a dentifrice, toothpaste, tooth powder, topical oral gel, mouth rinse, denture product, mouth spray, lozenge, oral tablet, or chewing gum.

Preferred oral care compositions also be in the form of dentifrices, such as toothpastes, tooth gels, and tooth powders. Components of such toothpaste and tooth gels generally include one or more of a dental abrasive (from about 6% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpaste or tooth gel further include one or more of an anticaries agent (from about 0.05% to about 0.3% as fluoride ion), and an anticalculus agent (from about 0.1% to about 13%). Tooth powders, of course, contain substantially all non-liquid components.

The oral care compositions of the present invention can be in the form of non-abrasive gels, including subgingival gels, which can be aqueous or non-aqueous. Aqueous gels generally include a thickening agent (from about 0.1% to about 20%), a humectant (from about 10% to about 55%), a flavoring agent (from about 0.04% to about 2%), a sweetening agent (from about 0.1% to about 3%), a coloring agent (from about 0.01% to about 0.5%), and the balance water. The compositions further comprise an anticaries agent (from about 0.05% to about 0.3% as fluoride ion), and an anticalculus agent (from about 0.1% to about 13%).

Other preferred oral care compositions are mouthwashes, including mouth sprays and mouth rinse. Components of such mouthwashes and mouth sprays typically include one or more of water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent (from about 0.03% to about 3%), and a coloring agent (from about 0.001% to about 0.5%). Such mouthwashes and mouth sprays also contain an anticaries agent (from about 0.05% to about 0.3% as fluoride ion) and an anticalculus agent (from about 0.1% to about 3%).

Other preferred oral care compositions of the subject invention are dental solutions including irrigation fluids. Chewing gum compositions typically include one or more of a gum base (from about 50% to about 99%), a flavoring agent (from about 0.4% to about 2%), and a sweetening agent (from about 0.01% to about 20%). Lozenges include discoid-shaped solids comprising a therapeutic agent in a flavored base. The base can be a hard sugar candy, glycerinated gelatin or combination of sugar with sufficient mucilage to give it form. Dental implements impregnated with the oral care present composition comprise an implement for contact with teeth and other tissues in the oral cavity. The dental implement can be impregnated fibers including dental floss or tape, chips, or strips and polymer fibers. Dental abrasives useful in the topical, oral carriers of the compositions of the subject invention include many materials. The material selected must be compatible within the present oral care composition that does not excessively abrade dentin. Suitable abrasives include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde. Another class of abrasives are thermosetting polymerized resins which include melamines, phenolics, ureas, melamine-ureas, melamine-formaldehydes, urea-formaldehyde, melamine-urea -formaldehydes, cross-linked epoxides, and cross-linked polyesters. Silica dental abrasives are preferred because of their unique benefits of exceptional dental cleaning and polishing performance without unduly abrading tooth enamel or dentine. The silica abrasive polishing materials have an average particle size ranging between about 0.1 to about 30 microns, and preferably from about 5 to about 15 microns. The abrasive can be precipitated silica or silica gels. Mixtures of abrasives can be used. The total amount of abrasive in dentifrice compositions of the subject invention preferably range from about 6% to about 70% by weight; toothpastes preferably contain from about 10% to about 50% of abrasives, by weight of the composition.

The present invention also provides a method for removing stains from teeth comprising contacting a subject's teeth with an oral care composition comprising: (a) an oral care acceptable carrier, and (b) at least about 0.1% by weight of a water-soluble polymer comprising a first monomer having hydrogen bonding/complexing properties to polyphenols, a second monomer having detergent properties, and a third monomer having hydrogen bonding/complexing properties to polyphenols, wherein the first monomer and the third monomer or polymers are the same or different, wherein the orally care acceptable carrier is a toothpaste, dentifrice, tooth powder, topical oral gel, mouth rinse, denture product, mouth spray, lozenge, oral tablet, chewing gum, or impregnated dental implement, wherein the oral care composition provides stain removal from teeth.

The present invention also provides methods for cleaning and polishing teeth and reducing the incidence of stain, plaque, and gingivitis and calculus on dental enamel. The method of use comprises contacting a subject's dental enamel surfaces and oral mucosa with the oral care compositions according to the present invention. The method of use can be by brushing with a dentifrice, rinsing with a dentifrice slurry, a mouth rinse, chewing a gum product, contacting a topical oral gel, mouth spray, or other form with the subject's teeth and oral mucosa. The subject can be a person or animal whose tooth surface contacts the oral composition.

Without wishing to be bound by theory for the removal of stains from teeth, applicants believe that hydrogen bond acceptors (e.g. pyrrolidone group from the vinyl pyrrolidone) bind to polyphenolic stains present in teeth by hydrogen bonding forming a polymer/polyphenol complex. Polyphenols are present in a variety of dietary products and consumption of these products causes deposition of staining material on teeth. The monomer group of this invention possessing detergent properties allows the polymer/polyphenol complex to become solubilized, lifting the stain off the surface of the tooth into the bulk aqueous media. If the polymer/polyphenol complex does not possess enough hydrophilicity, the complex will not lift-off the tooth surface. Conversely, if the polymer/polyphenol complex is not strong enough, the polymer will not be able bind to the stain to form the complex. While the carbonyl oxygen atom in vinylpyrrolidone is a strong hydrogen bond accepter, access to the oxygen atom is hindered due to the close proximity of the oxygen atom to the polymeric backbone. Applicants have found that extending the pyrrolidone group away from the polymeric backbone on a pendant group results in less steric hindrance and better access to the oxygen atom by a polyphenolic chromophore.

The polyphenols found in tooth stains, contain many phenolic groups, in different chemical environments, possessing different physical and chemical properties. In some cases, the first monomer and the third monomer are the same and provide the desired pyrrolidone binding to the polyphenols in the teeth to form the resulting pyrrolidone/polyphenolic complex on the surface of the teeth. In some cases, the first monomer and the third monomer are different, with similar but complimentary properties, to optimize the strength of the polymer/polyphenol complex formation.

The following non-limiting examples further illustrate the certain aspects of the present invention.

EXAMPLES

Example 1—Synthesis of VP/PEG-Me-MA/SHEMA (20/30/50)

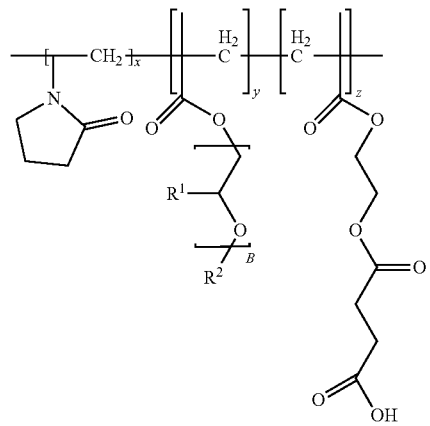

Feed one is prepared with 7.15 g vinyl pyrrolidone (VP); 48.28 g poly(ethylene glycol) methyl ether methacrylate (500 Mn) (PEG-Me-MA); 37.05 g mono-2-(Methacryloyloxy)ethyl succinate (SHEMA), and 41.27 g methyl ethyl ketone (MEK). Put 198.1 g MEK into the reactor and commence purging of the reaction vessel with nitrogen. Heat the reaction flask containing MEK to reflux—approximately ~78C. In a separate vessel prepare a mixture of Trigonox 25C 75 (1.0 g) and MEK (20 g). Label this vessel "Trigonox Solution". When the reaction flask has reached reflux temperature, begin adding Feed 1, drop-wise, in to the reaction vessel over a period of 180 minutes. After 15 minutes of monomer feed, add 2 g of the Trigonox solution into the reactor. Continue the drop-wise addition of Feed 1 over a period of approximately 165 minutes. While the monomers are feeding into the reactor, after 30 minutes charge 2.0 g of the Trigonox solution. After 45, 60, 75, 90, 105 and 120 minutes, charge 2.0 g Trigonox solution into the reactor. After 150 minutes, charge 2.0 g Trigonox solution into the reactor. At the completion of the monomer feeds, charge the reaction vessel with the remainder of the Trigonox solution. The reaction vessel is allowed to heat at reflux for an additional 180 minutes. Note: during the initiator shots, additional MEK was added to replace any that has volatilized. Cool the reaction vessel and leave the material in the reactor. This is the end of 'day one'. On 'day two', re-heat the vessel to reflux and charge with 2.5 g Trigonox 25C 75. Hold for 2 hours. Add an additional 2.5 g Trigonox 25C 75. Hold for 5 hours then cool reaction mixture.

Example 2—Synthesis of M-06/PEG-Me-MA/SHEMA (20/30/50)

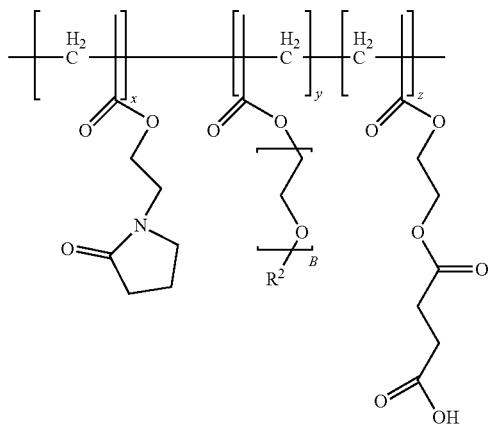

Feed one is prepared with 12.49 g hydroxyethylpyrolidone methacrylate (M-06); 47.53 g poly(ethylene glycol) methyl ether methacrylate (500 Mn) (PEG-Me-MA); 36.47 g. mono-2-(Methacryloyloxy)ethyl succinate (SHEMA), and 40.62 g methyl ethyl ketone (MEK). Put 195.00 g MEK into the reactor and commence purging of the reaction vessel with nitrogen. Heat the reaction flask containing MEK to reflux—approximately ~78C. In a separate vessel prepare a mixture of Trigonox 25C 75 (1.0 g) and MEK (20 g). Label this vessel "Trigonox solution". When the reaction flask has reached reflux temperature, begin adding Feed 1, drop-wise, in to the reaction vessel over a period of 180 minutes. After 15 minutes of monomer feed, add 2 g of the Trigonox solution into the reactor. Continue the drop-wise addition of Feed 1 over a period of approximately 165 minutes. While the monomers are feeding into the reactor, after 30 minutes charge 2.0 g of the Trigonox solution. After 45, 60, 75, 90, 105 and 120 minutes, charge 2.0 g Trigonox solution into the reactor. After 150 minutes, charge 2.0 g Trigonox solution into the reactor. At the completion of the monomer feeds, charge the reaction vessel with the remainder of the Trigonox solution. The reaction vessel is allowed to heat at reflux for an additional 180 minutes. Note: during the initiator shots, additional MEK was added to replace any that has volatilized. Cool the reaction vessel and leave the material in the reactor. This is the end of 'day one'. On 'day two', re-heat the vessel to reflux and charge with 2.5 g Trigonox 25C 75. Hold for 2 hours. Add an additional 2.5 g Trigonox 25C 75. Hold for 5 hours then cool reaction mixture.

Example 3—Synthesis of VP/PEG-Me-MA/M-06 (33/33/33)

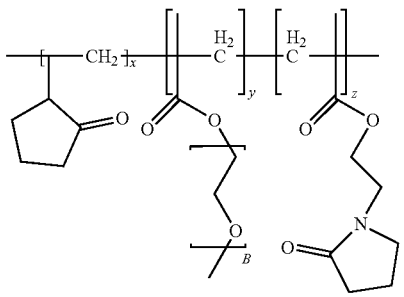

Feed one is prepared with 14.16 g vinyl pyrrolidone (VP); 25.10 g hydroxyethylpyrolidone methacrylate (M-06); 63.72 g poly(ethylene glycol) methyl ethermethacrylate (500 Mn) (PEG-Me-MA); and 49.01 g methyl ethyl ketone (MEK). Put 171.54 g MEK into the reactor and commence purging of the reaction vessel with nitrogen. Heat the reaction flask containing MEK to reflux—approximately ~78C. In a separate vessel prepare a mixture of Trigonox 25C 75 (1.0 g) and MEK (20 g). Label this vessel "Trigonox solution". When the reaction flask has reached reflux temperature, begin adding Feed 1, drop-wise, in to the reaction vessel over a period of 180 minutes. After 15 minutes of monomer feed, add 2 g of the Trigonox solution into the reactor. Continue the drop-wise addition of Feed 1 over a period of approximately 165 minutes. While the monomers are feeding into the reactor, after 30 minutes charge 2.0 g Trigonox solution. After 45, 60, 75, 90, 105 and 120 minutes, charge 2.0 g Trigonox solution into the reactor. After 150 minutes, charge 2.0 g Trigonox solution into the reactor. At the completion of the monomer feeds, charge the reaction vessel with the remainder of the Trigonox solution. The reaction vessel is allowed to heat at reflux for an additional 180 minutes. Note: during the initiator shots, additional MEK was added to replace any that has volatized. Cool the reaction vessel and leave the material in the reactor. This is the end of 'day one'. On 'day two', re-heat the vessel to reflux and charge with 2.5 g Trigonox 25C 75. Hold for 2 hours. Add an additional 2.5 g Trigonox 25C 75. Hold for 5 hours then cool reaction mixture.

Example 4—Synthesis of VA/PEG-Me-MA/SHEMA (20/30/50)

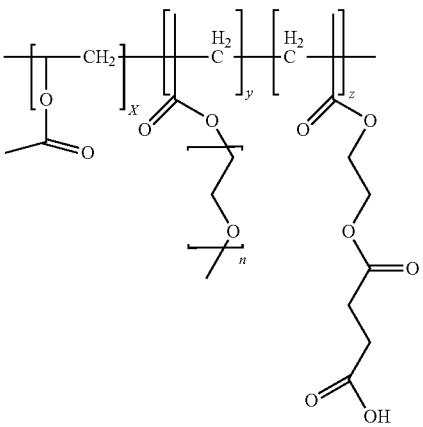

Feed one is prepared with 48.51 g poly(ethylene glycol) methyl ether methacrylate (500 Mn) (PEG-Me-MA); 37.22 g mono-2-(Methacryloyloxy)ethyl succinate (SHEMA), and 41.46 g methyl ethyl ketone (MEK). Put 5.57 g vinyl acetate (VA) and 200.00 g MEK into the reactor and commence purging of the reaction vessel with nitrogen. Heat the reaction flask containing MEK to reflux—approximately ~78C. In a separate vessel prepare a mixture of Trigonox 25C 75 (1.0 g) and MEK (20 g). Label this vessel "Trigonox Solution". When the reaction flask has reached reflux temperature, begin adding Feed 1, drop-wise, in to the reaction vessel over a period of 180 minutes. After 15 minutes of monomer feed, add 2 g of the Trigonox Solution into the reactor. Continue the drop-wise addition of Feed 1 over a period of approximately 165 minutes. While the monomers are feeding into the reactor, after 30 minutes charge 2.0 g of the Trigonox solution. After 45, 60, 75, 90, 105 and 120 minutes, charge 2.0 g Trigonox solution into the reactor. After 150 minutes, charge 2.0 g Trigonox solution into the reactor. At the completion of the monomer feeds, charge the reaction vessel with the remainder of the Trigonox solution. The reaction vessel is allowed to heat at reflux for an additional 180 minutes. Note: during the initiator shots, additional MEK was added to replace any that has volatilized. Cool the reaction vessel and leave the material in the reactor. This is the end of 'day one'. On 'day two', re-heat the vessel to reflux and charge with 2.5 g Trigonox 25C 75. Hold for 2 hours. Add an additional 2.5 g Trigonox 25C 75. Hold for 5 hours then cool reaction mixture.

Example 5—Synthesis of PEG-OMe-MA/SHEMA (50/50)

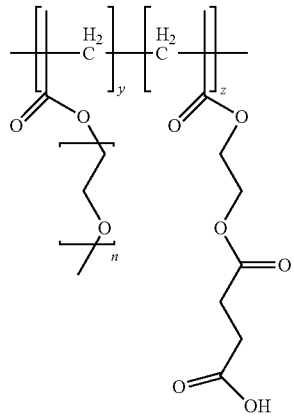

Feed one is prepared with 70.16 g poly(ethylene glycol) methyl ether methacrylate (500 Mn) (PEG-Me-MA); 32.30 g mono-2-(Methacryloyloxy)ethyl succinate (SHEMA), and 43.18 g methyl ethyl ketone (MEK). Put 188.53 g MEK into the reactor and commerce purging of the reaction vessel with nitrogen. Heat the reaction flask containing MEK to reflux—approximately ~78C. In a separate vessel prepare a mixture of Trigonox 25C 75 (1.0 g) and MEK (20 g). Label this vessel "Trigonox Solution". When the reaction flask has reached reflux temperature, begin adding Feed 1, drop-wise, in to the reaction vessel over a period of 180 minutes. After 15 minutes of monomer feed, add 2 g of the Trigonox Solution into the reactor. Continue the drop-wise addition of Feed 1 over a period of approximately 165 minutes. While the monomers are feeding into the reactor, after 30 minutes charge 2.0 g of the Trigonox solution. After 45, 60, 75, 90, 105 and 120 minutes, charge 2.0 g Trigonox solution into the reactor. After 150 minutes, charge 2.0 g Trigonox solution into the reactor. At the completion of the monomer feeds, charge the reaction vessel with the remainder of the Trigonox solution. The reaction vessel is allowed to heat at reflux for an additional 180 minutes. Note: during the initiator shots, additional MEK was added to replace any that has volatilized. Cool the reaction vessel and leave the material in the reactor. This is the end of 'day one'. On 'day two', re-heat the vessel to reflux and charge with 2.5 g Trigonox 25C 75. Hold for 2 hours. Add an additional 2.5 g Trigonox 25C 75. Hold for 5 hours then cool reaction mixture.

Example 6—Synthesis of VP/PEG-Me-MA (50/50)

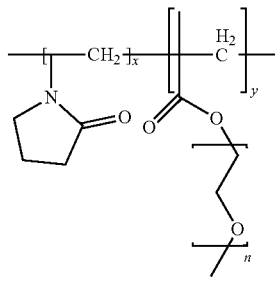

Feed one is prepared with 18.58 g vinyl pyrrolidone (VP); 83.60 g poly(ethylene glycol) methyl ether methacrylate (500 Mn) (PEG-Me-MA, and 60.02 methyl ethyl ketone (MEK). Put 163.8 g MEK into the reactor and commence purging of the reaction vessel with nitrogen. Heat the reaction flask containing MEK to reflux—approximately ~78C. In a separate vessel prepare a mixture of Trigonox 25C 75 (1.0 g) and MEK (20 g). Label this vessel "Trigonox solution". When the reaction flask has reached reflux temperature, begin adding Feed 1, drop-wise, in to the reaction vessel over a period of 180 minutes. After 15 minutes of monomer feed, add 2 g of the Trigonox solution into the reactor. Continue the drop-wise addition of Feed 1 over a period of approximately 165 minutes. While the monomers are feeding into the reactor, after 30 minutes charge 2.0 g of the Trigonox solution. After 45, 60, 75, 90, 105 and 120 minutes, charge 2.0 g Trigonox solution into the reactor. After 150 minutes, charge 2.0 g Trigonox solution into the reactor. At the completion of the monomer feeds, charge the reaction vessel with the remainder of the Trigonox solution. The reaction vessel is allowed to heat at reflux for an additional 180 minutes. Note: during the initiator shots, additional MEK was added to replace any that has volatilized. Cool the reaction vessel and leave the material in the reactor. This is the end of 'day one'. On 'day two', re-heat the vessel to reflux and charge with 2.5 g Trigonox 25C 75. Hold for 2 hours. Add an additional 2.5 g Trigonox 25C 75. Hold for 5 hours then cool reaction mixture.

Example 7—Synthesis of PEG-Me-MA/M-06 (50/50)

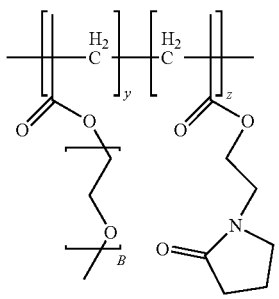

Feed one is prepared with 29.04 g hydroxyethylpyrolidone methacrylate (M-06); 73.72 g poly(ethylene glycol) methyl ether methacrylate (500 Mn) (PEG-Me-MA), and 52.93 g methyl ethyl ketone (MEK). Put 170.12 g MEK into the reactor and commence purging of the reaction vessel with nitrogen. Heat the reaction flask containing MEK to reflux—approximately ~78C. In a separate vessel prepare mixture of Trigonox 25C 75 (1.0 g) and MEK (20 g). Label this vessel "Trignox solution". When the reaction flask has reached reflux temperature, begin adding Feed 1, drop-wise, in to the reaction vessel over a period of 180 minutes. After 15 minutes of monomer feed, add 2 g of the Trigonox solution into the reactor. Continue the drop-wise addition of Feed 1 over a period of approximately 165 minutes. While the monomers are feeding into the reactor, after 30 minutes charge 2.0 g of the Trigonox solution. After 45, 60, 75, 90, 105 and 120 minutes, charge 2.0 g Trigonox solution into the reactor. After 150 minutes, charge 2.0 g Trigonox solution into the reactor. At the completion of the monomer feeds, charge the reaction vessel with the remainder of the Trigonox solution. The reaction vessel is allowed to heat at reflux for an additional 180 minutes. Note: during the initiator shots, additional MEK was added to replace any that has volatilized. Cool the reaction vessel and leave the material in the reactor. This is the end of 'day one'. On 'day two', re-heat the vessel to reflux and charge with 2.5 g Trigonox 25C 75. Hold for 2 hours. Add an additional 2.5 g Trigonox 25C 75. Hold for 5 hours then cool reaction mixture.

Example 8—Toothpaste Formulations Containing Inventive Polymers

In this example, Formulations A-D were prepared for toothpaste formulation.

| Ingredient | Formulation W/W (%) | | | |
|---|---|---|---|---|
| | 8A | 8B | 8C | 8D |
| Water | q.s. | q.s. | q.s. | q.s. |
| Glycerin | 20 | 20 | 20 | 20 |
| Sorbitol solution (70%) | 20 | 20 | 20 | 20 |
| CMC | 1.5 | 1.5 | 1.5 | 1.5 |
| Sodium saccharine | 0.2 | 0.2 | 0.2 | 0.2 |
| Sodium fluoride | 0.24 | 0.24 | 0.24 | 0.24 |
| Abrasive silica | 20 | 20 | 20 | 20 |
| Flavor | 1.5 | 1.5 | 1.5 | 1.5 |
| SLS | 2 | 2 | 2 | 2 |
| VP/PEG-OMe-MA/SHEMA (20:30:50) | 2 | 2 | 2 | 2 |
| Sodium pyrophosphate | 3 | — | — | 3 |
| Sodium tripolyphosphate | — | 5 | — | — |
| Potassium nitrate | — | — | 5 | — |
| Zinc citrate dihydrate | — | — | — | 2 |
| Totals: | 100 | 100 | 100 | 100 |

Example 9—Mouthwash Formulations Containing Inventive Polymers

In this example, Formulations A-D were prepared for mouthwash formulations.

| Ingredient | Formulation W/W (%) | | | |
|---|---|---|---|---|
| | 9A | 9B | 9C | 9D |
| Water | q.s. | q.s. | q.s. | q.s. |
| Glycerin | 10 | 10 | 10 | 10 |
| Ethanol | 16 | — | — | 16 |
| Sorbitol 70% solution | — | 7 | 7 | — |
| Sodium saccharine | 0.05 | 0.05 | 0.05 | 0.05 |
| Flavor | 0.15 | 0.15 | 0.15 | 0.15 |
| VP/PEG-OMe-MA (50:50) | 1 | 1 | 1 | 1 |
| Sodium pyrophosphate | 3 | 3 | 1 | — |
| Cetylpyridinium chloride | — | — | — | 0.07 |
| Hydrogen peroxide | — | — | 1.5 | — |
| Sodium fluoride | — | 0.05 | — | — |
| Poloxomer 407 | 0.25 | 0.2 | — | 0.2 |
| PEG-60 Hydrogenated castor Oil | — | 0.2 | — | — |
| Polysorbate 80 | — | — | 0.15 | 0.15 |
| Benzoic acid | 0.15 | 0.15 | — | 0.15 |
| Sodium benzoate | 0.15 | 0.15 | — | 0.15 |
| Totals: | 100 | 100 | 100 | 100 |

Example 10—Anhydrous/Very Low Water Toothpaste

| Ingredient | Wt % |
|---|---|
| VP/PEG-OMe-MA/SHEMA (20/30/50) | 2.0 |
| Glycerin | 48.21 |
| Propylene Glycol | 9.6 |
| PEG-400 | 7.0 |
| Xanthan Gum | 0.2 |
| Iota Carrageenan | 0.4 |
| Sodium fluoride | 0.24 |
| Abrasive Silica | 20 |
| Thickening Silica | 2.0 |
| Titanium Dioxide | 0.3 |
| Sodium Lauryl Sulfate | 1.5 |

| Ingredient | Wt % |
| --- | --- |
| Peppermint Oil | 1.0 |
| Sodium Saccharin | 0.3 |
| Disodium Pyrophosphate | 1.25 |
| Tetrasodium Pyrophosphate | 1.5 |
| Water | 4.5 |
| Total | 100 |

Example 11—Anhydrous Toothpaste

| Ingredient | Wt % |
| --- | --- |
| VP/PEG-OMe-MA/SHEMA (20/30/50) | 2 |
| Propylene Glycol, USP/NF | 33.21 |
| PEG 12, USP/NF | 12 |
| PEG/PPG 116/66 | 12.7 |
| Polyplasdone XL-10 | 7 |
| Glycerin, USP 99.5% | 5 |
| Abrasive Silica | 20 |
| Thickening Silica | 2 |
| Sodium Saccharin | 0.3 |
| Sodium fluoride | 0.24 |
| Disodium pyrophosphate | 1.25 |
| Tetrasodium pyrophosphate | 1.5 |
| Titanium dioxide | 0.3 |
| sodium lauryl sulfate, USP/NF | 1.5 |
| Peppermint Oil | 1 |
| Total | 100 |

Example 12—Chewing Gum

| Ingredient | Wt % |
| --- | --- |
| Gum base | 37 |
| Sorbitol | 45 |
| Mannitol | 10 |
| Flavor | 4 |
| Glycerin | 1.5 |
| Lecithin | 0.2 |
| VP/PEG-OME-MA/SHEMA | 2 |
| Sucralose | 0.3 |
| Total | 100 |

Example 13—Hard Candy Lozenge

| Ingredient | Wt % |
| --- | --- |
| Isomalt | 97.3 |
| Flavor | 0.5 |
| VP/PEG-OMe-MA (50:50) | 2 |
| Sucralose | 0.2 |
| Total | 100 |

Example 14—Compressed Tablet Lozenge

| Ingredient | Wt % |
| --- | --- |
| Sorbitol | 96 |
| Flavor | 0.5 |
| Magnesium Stearate | 0.5 |
| Silica | 1 |
| VP/PEG-OMe-MA/SHEMA | 2 |
| Total | 100 |

Example 15—Thin Film Mouth Strip

| Ingredient | Wt % |
| --- | --- |
| Sodium Alginate | 94.3 |
| Plasticizer (glycerin) | 3 |
| Flavor | 0.5 |
| VP/PEG-OMe-MA (50:50) | 2 |
| Sucralose | 0.2 |
| Total | 100 |

Example 16—Binding of a Selected Polyphenol Staining Agent to No Polymer, Polyvinylpyrrolidone, and Vinylpyrrolidone/Hydroxyethylpyrolidone Methacrylate (Polymer B, p-VP/M-06/30/70)

The binding of polyvinylpyrrolidone and vinylpyrrolidone/hydroxyethylpyrolidone methacrylate (Polymer B, p-VP/M-06/30/70) to a common polyphenolic staining agent in solution was measured. The test results show that polyvinylpyrrolidone, vinylpyrrolidone/hydroxyethylpyrolidone methacrylate binds more tightly to the polyphenolic compound than polyvinylpyrrolidone (PVP-K15) (see FIG. 1). In this experiment, lower free (available) polyphenol indicates better polymer/polyphenol binding.

Vinylpyrrolidone/hydroxyethylpyrolidone methacrylate 30/70 (PVP/M-06) was formulated into a model toothpaste and tested for its' ability to whiten tea-stained, artificial teeth. The performance of vinylpyrrolidone/hydroxyethylpyrolidone methacrylate 30/70 proved to be poorer than the toothpaste base, without polymer and was, in fact, darker than the original stain. This result was surprising, given the superior binding to the polyphenol staining agent shown by the poly(VP/M-06) 30170 polymer.

Clearly, there was more to cleaning of tea stained artificial teeth than just the ability to hydrogen bond to the polyphenolic chromophores. For effective cleaning on artificial teeth, the polymer/chromophore complex must also be able to lift off of the surface—becoming solubilized into the aqueous toothpaste solution.

Example 17—Cleaning Results using Tea Stained, Artificial Teeth

To explore this theory further, additional copolymers were synthesized with either vinyl pyrrolidone (VP) or, 2-hydroxyethyl-2-pyrrolidone methacrylate (M-06) monomers as one of the hydrogen bonding groups. The other monomers included groups such as poly(ethylene glycol) methyl ether methacrylate (PEG-OMe-MA) and, mono-2-(methacryloyloxy) ethyl succinate (SHEMA). These co-polymer variants are shown, below.

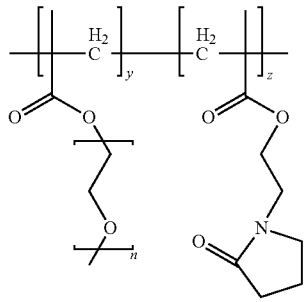

PEG-OMe-MA/MO-6 (1:1)

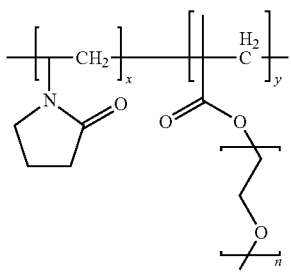

VP/PEG-OMe-MA (1:1)

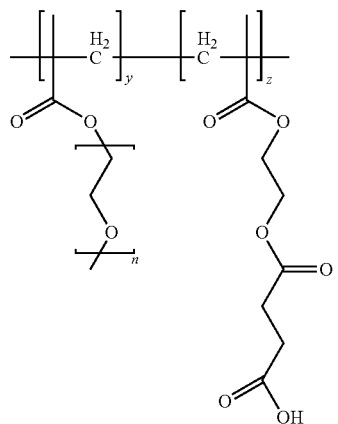

PEG-OMe-MA/SHEMA (1:1)

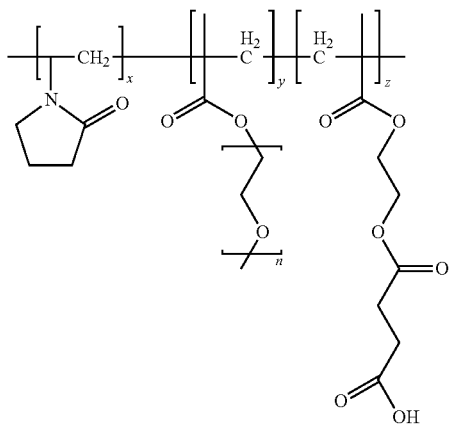

VP/PEG-OMe-MA/SHEMA (20:30:50)

-continued

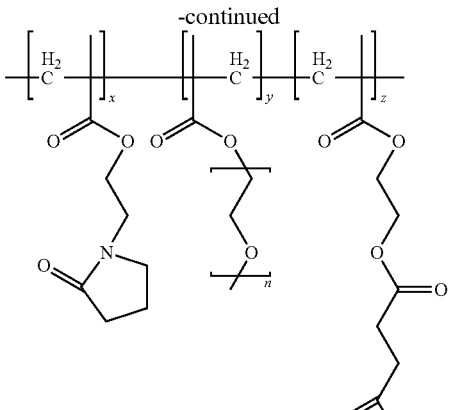

MO-6/PEG-OMe-MA/SHEMA (20/30/50)

Figure 2:
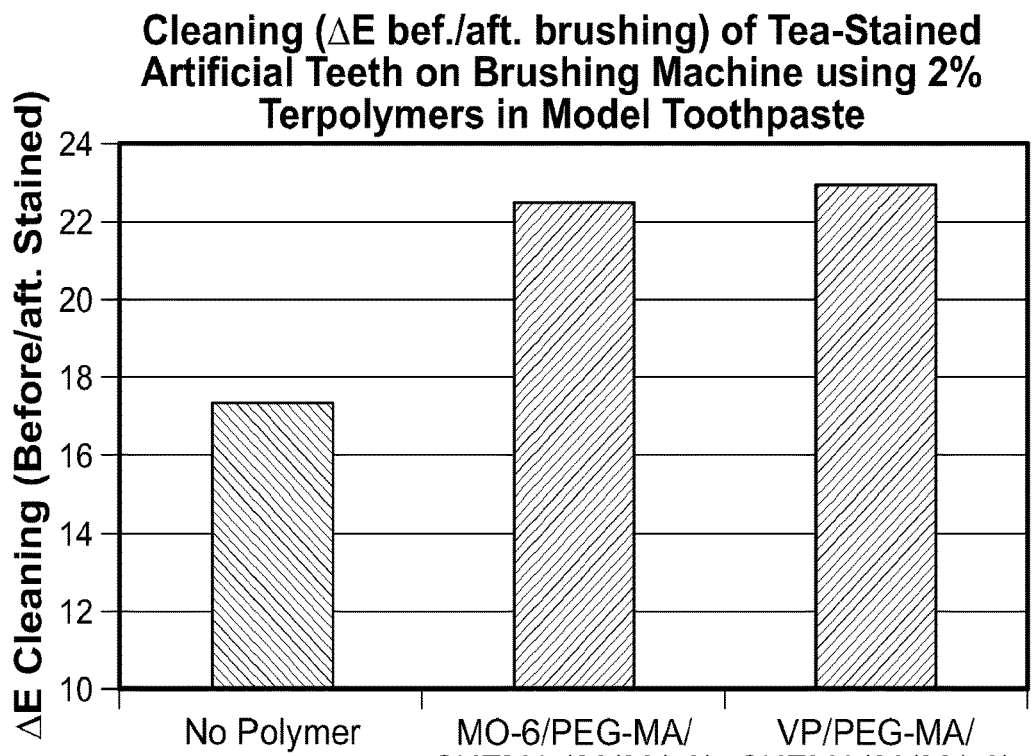
FIG. 2: Cleaning results using terpolymers.
Figure 3:
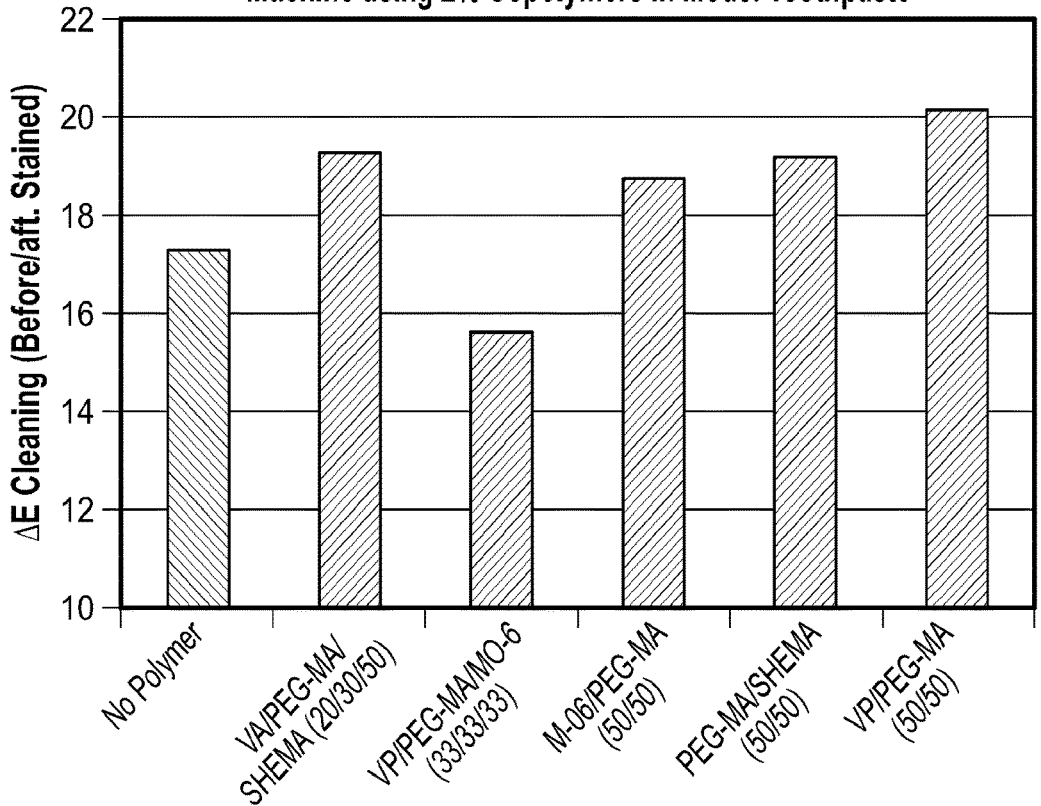
FIG. 3: Cleaning results using terpolymers and copolymers.

The results of artificial teeth cleaning experiments using these terpolymers and copolymers polymers are shown in FIGS. 2 and 3.

The CIE L*a*b* color space uses the equation $\Delta E = \sqrt{(L_2-L_1)^2+(a_2-a_1)^2+(b_2-b_1)^2}$ to determine the color difference between distinct color results, where $\Delta E$ is referred to as the E value, or color difference. The value L, known as luminosity, ranges from zero to one hundred (0=Black; 100=Pure White) for the black/white component of color, while a and b indicate the green/red and blue/yellow axes of the color space, respectively.

The results of the brushing study show that the most effective cleaning (brushing artificial tea-stained teeth in model toothpaste formulations) was seen using a copolymer containing a combination of three monomers: (1) VP or M-06, (2) PEG-MA and, (3) SHEMA monomers (FIG. 2).

FIG. 3 shows the cleaning results of the copolymer combinations. While showing good cleaning efficacy, the VP/PEG-MA (50:50) co-polymer, was not as effective as the VP/PEG-MA/SHEMA or the M-06/PEG-MA/SHEMA terpolymers (shown in FIG. 2).

The poor cleaning performance of the VP/PEG-MA/M-06 (33:33:33) terpolymer (poorer than the toothpaste base, without polymer), seen in FIG. 3, may be likened to the poor cleaning seen by VP/M-06 (30/70) polymer, described earlier. Like the VP/M-06 (30/70) polymer, the VP/PEG-MA/M-06 (33:33:33) polymer does not appear to have the proper balance of solubility and surfactancy (along with hydrogen bonding ability).

Figure 4:
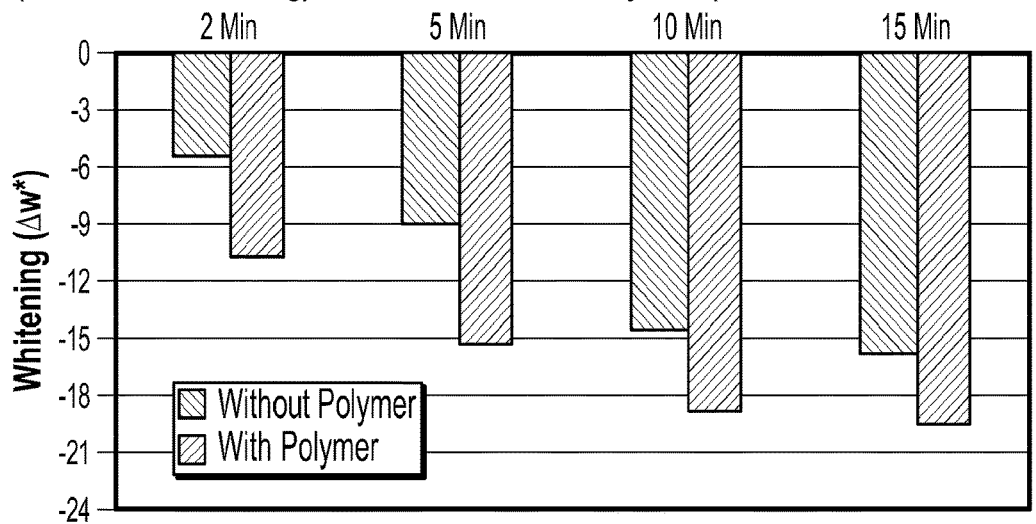
FIG. 4: Cleaning results for aqueous toothpaste formulation with and without 2% VP/PEG-OMe-MA/SHEMA (20/30/50) terpolymer.
Figure 5:
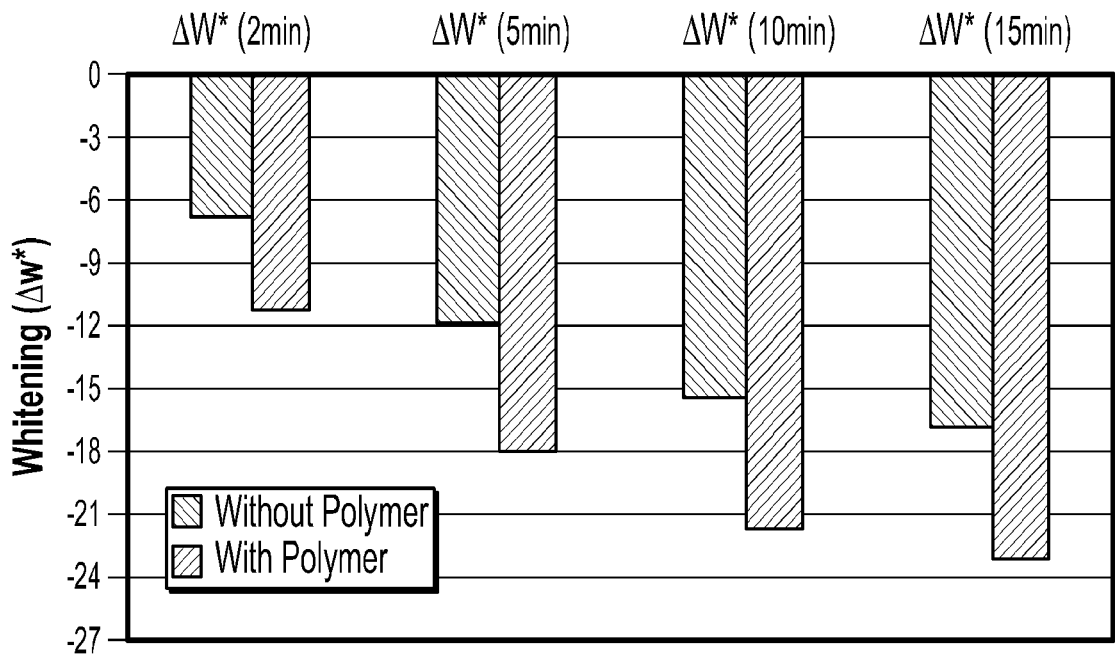
FIG. 5: Cleaning results of anhydrous-based toothpaste formulation with and without 2% VP/PEG-OMe-MA/SHEMA (20/30/50) terpolymer.

Additional whitening studies on stained bovine teeth were conducted using aqueous and non-aqueous toothpaste formulations with and without the addition of the VP/PEG-OMe-MA/SHEMA (20:30:50) terpolymer variant. Differences in whitening of the stained bovine teeth before and after brushing were determined using changes in the whitness index and were determined after 2, 5, 10, and 15-minute brushing time intervals. The results are shown in FIGS. 4 and 5.

The whitening of bovine teeth is expressed using changes in the whitening index (W*), which compares the measured L*a*b* values (in the CIE color space) to a theoretical pure white value (where L=100 and, a* and b*=0). It is calculated as follows: $W^*=[(a^*)^2+(b^*)^2+(L-100)^2]^{1/2}$. Changes in the closeness to white, before/after treatment ($\Delta W^*$) is defined as: $\Delta W^* = W^*$ (treatment) $- W^*$ (baseline). In this system a more negative $\Delta W^*$ is indicative of better whitening—with a value of 0 indicative of no change and, a positive value indicative of a darkening of the original stain, after treatment.

The surfactancy of the VP/PEG-OMe-MA/SHEMA (20/30/50) and the M-06/PEG-Ome-MA/SHEMA (20/30/50) terpolymers is demonstrated by a reduction in the air/liquid surface tension of these polymers dissolved in water (see Table 1).

TABLE 1

| Polymer (2% Solution, in water, pH 7.0) | Surface Tension (dyne-cm) |
|---|---|
| VP/PEG/SHEMA (20/30/50) | 49.7 |
| MO-6/PEG/SHEMA (20/30/50) | 45.6 |

According to one of the embodiment of the invention, SHEMA monomer also has the ability to act as a hydrogen bond acceptor. Hydrogen bonding is most likely to occur at both of the carbonyl oxygen groups on the pendant succinic acid ester. The location of the succinic acid ester group (away from the polymer backbone), is also expected to improve the hydrogen bonding ability of this group.

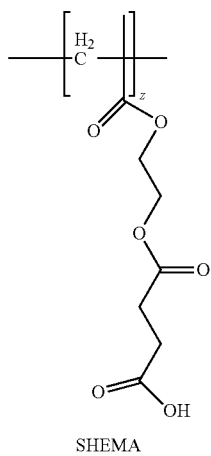

SHEMA

The cleaning data from FIG. 2 and FIG. 3 indicates that each of the three monomers, (1) VP or M-06, (2) PEG-OMe-MA and, (3) SHEMA, are needed for optimal tea stain removal from artificial teeth and that they all appear to contribute to the cleaning performance of the terpolymer.

The discovery that multiple monomer groups on the polymer are needed for optimal cleaning of tea-stained artificial teeth is unexpected. The mechanism of polyphenol stain removal from the surface of teeth is complicated with: hydrogen bonding ability, surfactancy, and solubility of the resultant polymer/chromophore complex all being important.

Two sub-sets of terpolymers: VP/PEG-OMe-MA/SHEMA and M-06/PEG-OMe/SHEMA are effective at removing tea-stains from artificial teeth. The role that each of the monomer groups plays is mentioned, below.
  i) VP is a good hydrogen bonder and has good/moderate water solubility.
  ii) M-06 group is also a good hydrogen bonder, with less water solubility than PVP and Should also provide surface tension lowering due to some hydrophobicity, helping to increase surface activity.
  iii) PEG-OMe-MA group possesses very good water solubility, good surfactancy/detergency and, also has moderate hydrogen bonding ability (from the ether oxygens).
  iv) SHEMA group is an effective hydrogen bonder and is somewhat hydrophobic, providing surface tension reduction (increased surface activity).

While a number of embodiments of this invention have been represented, it is apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

We claim:

1. The water-soluble or water-dispersible polymer having a structure selected from the group consisting of:

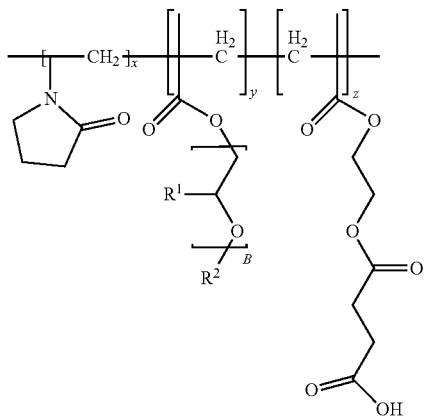

wherein x=5-90, y=5-90, z=5-90, mole %, and n is an integer ranging from 1 to about 100, and, $R_1$, $R_2$=H or $CH_3$,

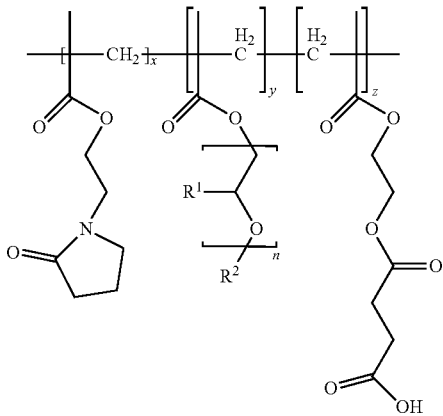

wherein x=5-90, y=5-90, z=5-90, mole %, and n is an integer ranging from 1 to about 100, and, $R_1$, $R_2$=H or $CH_3$,

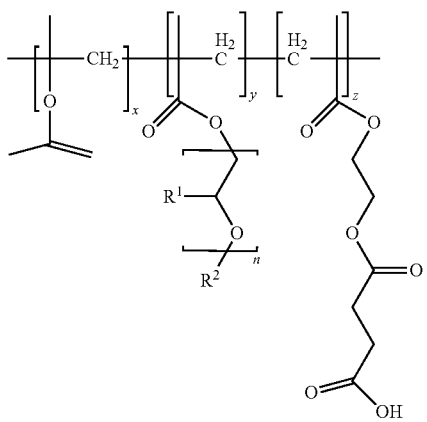

wherein x=5-90, y=5-90, z=5-90, mole %, and n is an integer ranging from 1 to about 100, and, $R_1$, $R_2$=H or $CH_3$,

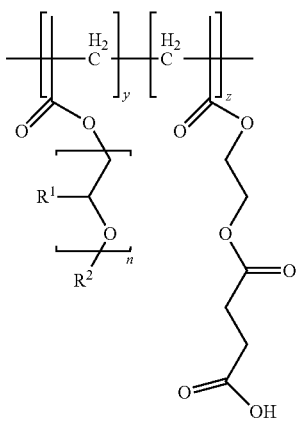

wherein x=5-95, y=5-95, mole %, and n is an integer ranging from 1 to about 100, and, $R_1$, $R_2$=H or $CH_3$,

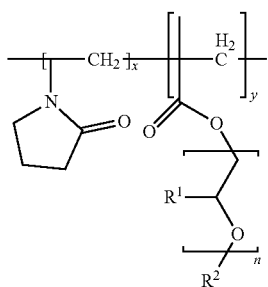

wherein x=5-95, y=5-95, mole %, and n is an integer ranging from 1 to about 100, and, $R_1$, $R_2$=H or $CH_3$, and

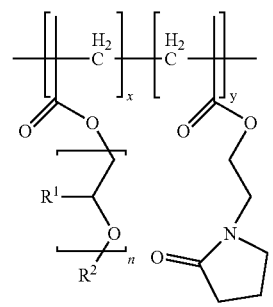

wherein x=5-95, y=5-95, mole %, and n is an integer ranging from 1 to about 100, and, $R_1$, $R_2$=H or $CH_3$, and wherein the water-soluble or water-dispersible polymeric structures has a molecular weight of less than about 1,000,000 Daltons.

2. The water-soluble or water-dispersible polymer according to claim 1, wherein the structure of the polymer is selected from the group consisting of:

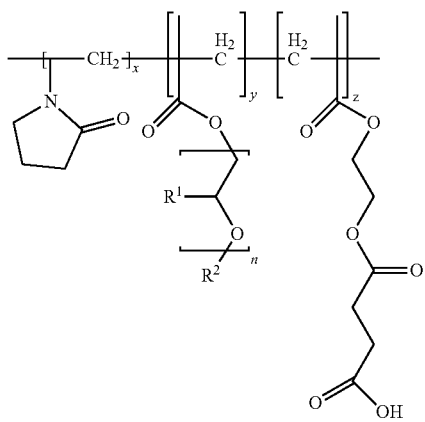

wherein x=5-90, y=5-90, z=5-90, mole %, and n is an integer ranging from 1 to about 100, and, $R_1$, $R_2$=H or $CH_3$,

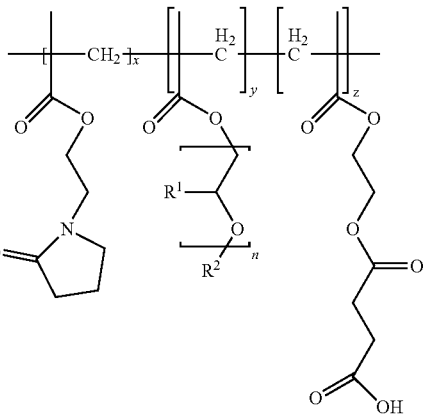

wherein x=5-90, y=5-90, z=5-90, mole %, and n is an integer ranging from 1 to about 100, and, $R_1$, $R_2$=H or $CH_3$, and

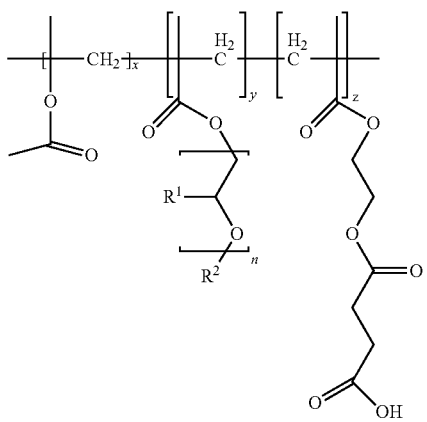

wherein x=5-90, y=5-90, z=5-90, mole %, and n is an integer ranging from 1 to about 100, and, $R_1$, $R_2$=H or $CH_3$.

3. The water-soluble or water-dispersible polymer according to claim 1, wherein the structure of the polymer is selected from the group consisting of:

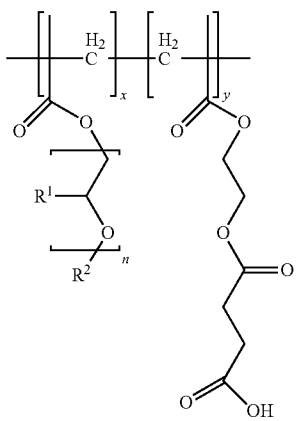

wherein x=5-95, y=5-95, mole %, and n is an integer ranging from 1 to about 100, and, $R_1$, $R_2$=H or $CH_3$,

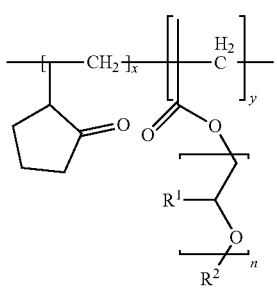

wherein x=5-95, y=5-95, mole %, and n is an integer ranging from 1 to about 100, and, $R_1$, $R_2$=H or $CH_3$, and

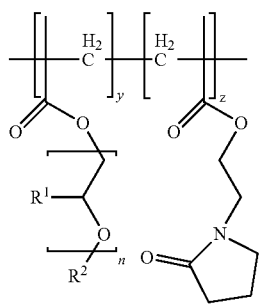

wherein x=5-95, y=5-95, mole %, and n is an integer ranging from 1 to about 100, and, $R_1$, $R_2$=H or $CH_3$.

4. The water-soluble or water-dispersible polymer according to claim 1, wherein the structure of the polymer is

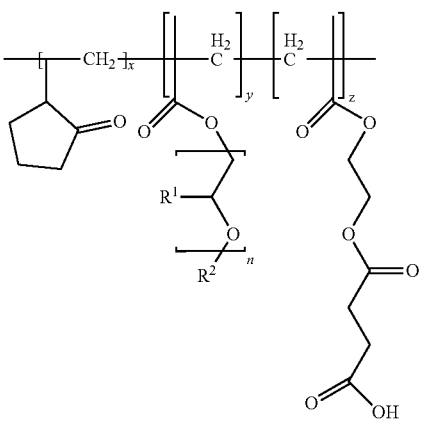

wherein x=5-90, y=5-90, z=5-90, mole %, and n is an integer ranging from 1 to about 100, and, $R_1$, $R_2$=H or $CH_3$ or

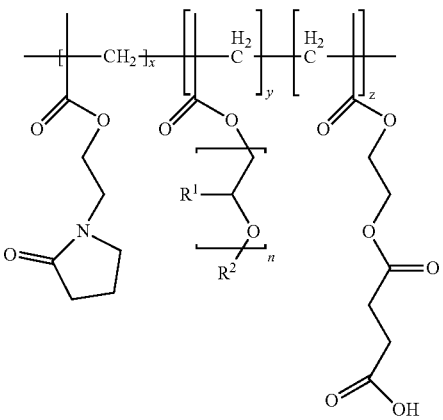

wherein x=5-90, y=5-90, z=5-90, mole %, and n is an integer ranging from 1 to about 100, and, $R_1$, $R_2$=H or $CH_3$.

5. An oral care composition comprising: (a) an oral care acceptable carrier, and (b) at least about 0.1% by weight of a water-soluble or water dispersible polymer selected from the group consisting of:

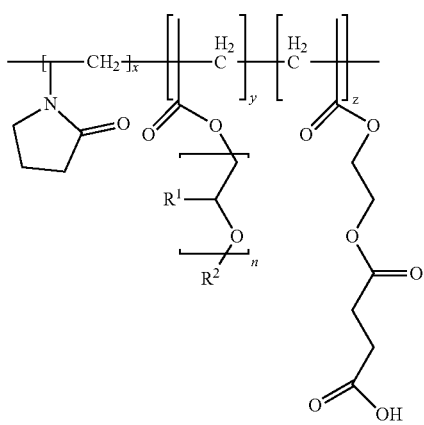

wherein x=5-90, y=5-90, z=5-90, mole %, and n is an integer ranging from 1 to about 100, and, $R_1$, $R_2$=H or $CH_3$,

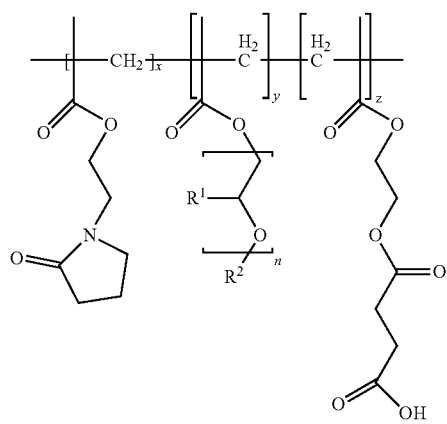

wherein x=5-90, y=5-90, z=5-90, mole %, and n is an integer ranging from 1 to about 100, and, $R_1$, $R_2$=H or $CH_3$,

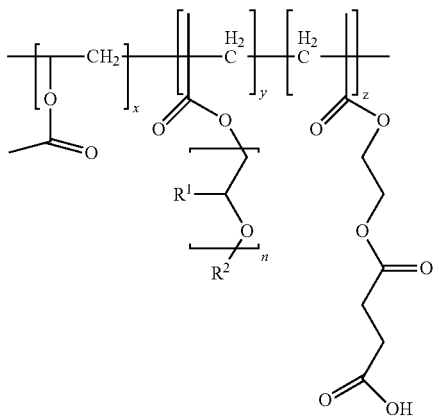

wherein x=5-90, y=5-90, z=5-90, mole %, and n is an integer ranging from 1 to about 100, and, $R_1$, $R_2$=H or $CH_3$,

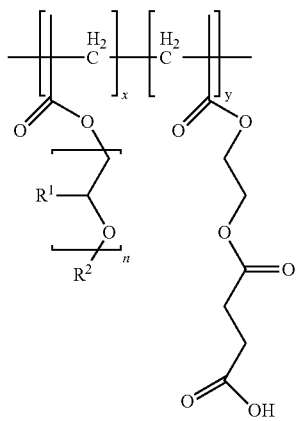

Wherein x=5-95, y=5-95, mole %, and n is an integer ranging from 1 to about 100, and, $R_1$, $R_2$=H or $CH_3$,

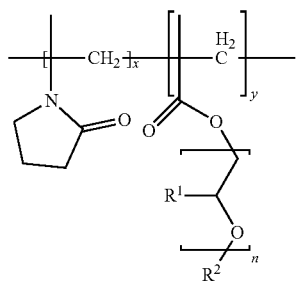

wherein x=5-95, y=5-95, mole %, and n is an integer ranging from 1 to about 100, and, $R_1$, $R_2$=H or $CH_3$, and

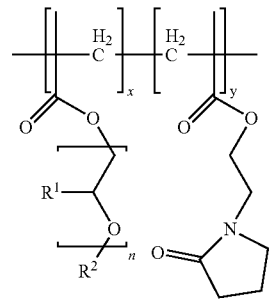

wherein x=5-95, y=5-95, mole %, and n is an integer ranging from 1 to about 100, and, $R_1$, $R_2$=H or $CH_3$:

wherein the oral care acceptable carrier is a toothpaste, dentifrice, tooth powder, topical oral gel, mouth rinse, denture product, mouth spray, lozenge, oral tablet, chewing gum, fast-dissolving films, strips, or impregnated dental implement, wherein the composition provides stain removal from teeth;

wherein the water-soluble polymer is present in an amount of about 2%, by weight, and has an air/liquid surface tension in water is below about 60 dynes/cm, and wherein the water-soluble or water-dispersible polymeric structures has a molecular weight of less than about 1,000,000 Daltons.

6. The oral care composition according to claim 5, wherein the composition further comprises at least one of a chelating agent, a bleaching agent, a fluoride providing agent, an ionic or non-ionic surfactant, an abrasive agent, an antibacterial agent, a desensitizing agent, and mixtures thereof.

7. A method for removing stains from teeth comprising contacting a subject's teeth with an oral care composition comprising: (a) an oral care acceptable carrier, and (b) at least about 0.1% by weight of a water-soluble polymer is selected from the group consisting of:

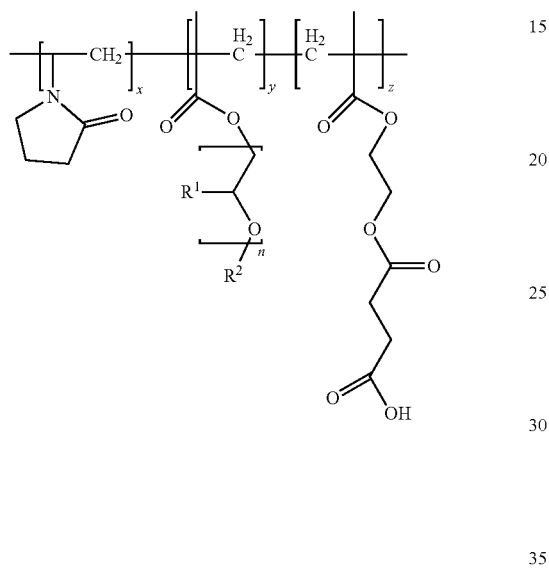

wherein x=5-90, y=5-90, z=5-90, mole %, and n is an integer ranging from 1 to about 100, and, $R_1$, $R_2$=H or $CH_3$,

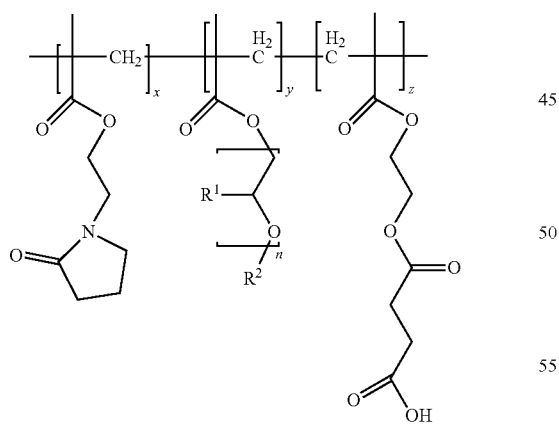

wherein x=5-90, y=5-90, z=5-90, mole %, and n is an integer ranging from 1 to about 100, and, $R_1$, $R_2$=H or $CH_3$,

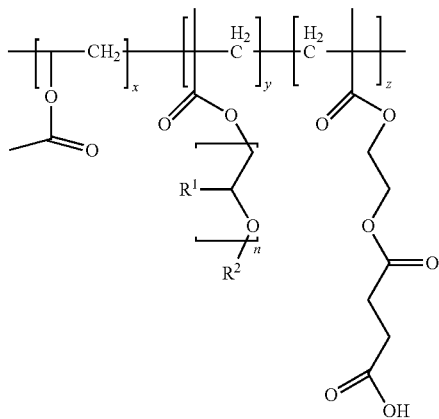

wherein x=5-90, y=5-90, z=5-90, mole %, and n is an integer ranging from 1 to about 100, and, $R_1$, $R_2$=H or $CH_3$,

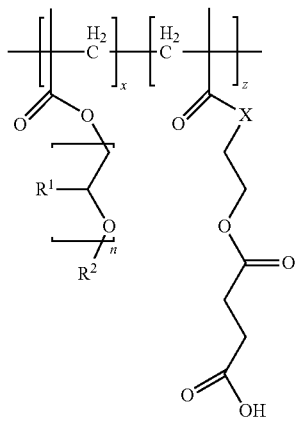

wherein x=5-95, y=5-95, mole %, and n is an integer ranging from 1 to about 100, and, $R_1$, $R_2$=H or $CH_3$,

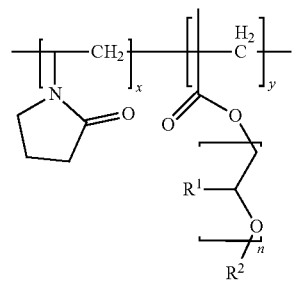

wherein x=5-95, y=5-95, mole %, and n is an integer ranging from 1 to about 100, and, $R_1$, $R_2$=H or $CH_3$, and

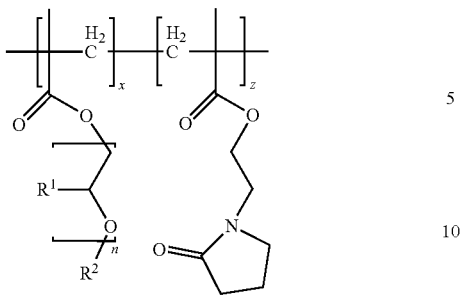

wherein x=5-95, y=5-95, mole %, and n is an integer ranging from 1 to about 100, and, $R_1$, $R_2$=H or $CH_3$;

wherein the water-soluble or water-dispersible polymeric structures has a molecular weight of less than about 1,000,000 Daltons, and wherein the oral care acceptable carrier is a toothpaste, dentifrice, tooth powder, topical oral gel, mouth rinse, denture product, mouth spray, lozenge, oral tablet, chewing gum, or impregnated dental implement, wherein the oral care composition provides stain removal from teeth.

* * * * *